(12) United States Patent
Berndt et al.

(10) Patent No.: US 9,592,308 B2
(45) Date of Patent: *Mar. 14, 2017

(54) METHOD FOR PRODUCTION OF F-18 LABELED AMYLOID BETA LIGANDS

(71) Applicant: PIRAMAL IMAGING SA, Matran (CH)

(72) Inventors: Mathias Berndt, Berlin (DE); Matthias Friebe, Berlin (DE); Fabrice Samson, Seoul (KR); Rainer Braun, Berlin (DE); Gunnar Garke, Haan (DE); Marianne Patt, Leipzig (DE); Andreas Schildan, Leipzig (DE); Christoph Smuda, Schlieren (CH)

(73) Assignee: PIRAMAL IMAGING SA, Matran (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/062,604

(22) Filed: Mar. 7, 2016

(65) Prior Publication Data

US 2016/0184465 A1 Jun. 30, 2016

Related U.S. Application Data

(63) Continuation of application No. 13/702,007, filed as application No. PCT/EP2011/058820 on May 30, 2011, now abandoned.

(30) Foreign Application Priority Data

Jun. 4, 2010 (EP) ...................................... 10164949

(51) Int. Cl.
*A61K 51/04* (2006.01)
*A61K 51/12* (2006.01)
(Continued)

(52) U.S. Cl.
CPC .......... *A61K 51/04* (2013.01); *A61K 51/0455* (2013.01); *A61K 51/121* (2013.01);
(Continued)

(58) Field of Classification Search
None
See application file for complete search history.

(56) References Cited

U.S. PATENT DOCUMENTS 5,723,103 A * 3/1998 de Paulis ........... A61K 51/0455
424/1.85
7,807,135 B2 10/2010 Kung et al.
(Continued)

FOREIGN PATENT DOCUMENTS

WO 2006066104 A2 6/2006

OTHER PUBLICATIONS

Ribeiro et al., "Reevaluation of Ethanol as Organic Modifier for Use in HPLC-RP Mobile Phases", J. Braz. Chem. Soc., vol. 15, 300-306, 2004.*
(Continued)

*Primary Examiner* — Jianfeng Song
(74) *Attorney, Agent, or Firm* — Millen White Zelano and Branigan, PC; John Sopp; Anthony Zelano

(57) ABSTRACT

This invention relates to methods, which provide access to [F-18]fluoropegylated (aryl/heteroaryl vinyl)-phenyl methyl amine derivatives.

14 Claims, 10 Drawing Sheets

(51) Int. Cl.
   *C07B 59/00*     (2006.01)
   *C07C 213/08*    (2006.01)
(52) U.S. Cl.
   CPC ............ *C07B 59/00* (2013.01); *C07C 213/08* (2013.01); *C07B 2200/05* (2013.01)

(56) References Cited

U.S. PATENT DOCUMENTS

| | | | |
|---|---|---|---|
| 2006/0269473 A1 | 11/2006 | Kung et al. | |
| 2010/0113763 A1* | 5/2010 | Moon | C07B 59/002 536/28.54 |
| 2010/0266500 A1 | 10/2010 | Kung et al. | |

OTHER PUBLICATIONS

International Search Report for PCT/EP2011/058820 dated Sep. 30, 2011.
Written Opinion for PCT/EP2011/058820 dated Dec. 4, 2012.
S. R. Choi et al. "Preclinical Properties of 18F-AV-45: A PET Agent for A Plaques in the Brain" The Journal of Nuclear Medicine, vol. 50, No. 11, (Oct. 16, 2009) pp. 1887-1894.
Zhang et al. "F-18 Polyethyleneglycol stilbenes as PET imaging agents targeting Abeta aggregates in the brain" Nuclear Medicine and Biology, Elsevier, vol. 32, No. 8, (Nov. 1, 2005) pp. 799-809.
Official Action dated Feb. 6, 2014, related to corresponding Eurasian Patent Application No. 201201645.
Official Action mailed Mar. 20, 2014, related to corresponding Chinese Patent Application No. 201180027675.X.
Seok Rye Choi et al. "Preclinical Properties of 18F-AV-45: A PET Agent for Aβ Plaques in the Brain" The Journal of Nuclear Medicine, [2009], vol. 50, No. 11, pp. 1887-1894.
Shilin Yu "High Performance Liquid Chromatography Method and Application" (second edition), Chemical Industry Publishing House, [2005], pp. 82-84.

* cited by examiner

METHOD FOR PRODUCTION OF F-18 LABELED AMYLOID BETA LIGANDS

FIELD OF INVENTION

This invention relates to methods, which provide access to [F-18]fluoropegylated (aryl/heteroaryl vinyl)-phenyl methyl amine derivatives.

BACKGROUND

Alzheimer's Disease (AD) is a progressive neurodegenerative disorder marked by loss of memory, cognition, and behavioral stability. AD is defined pathologically by extracellular senile plaques comprised of fibrillar deposits of the beta-amyloid peptide (Aβ) and neurofibrillary tangles comprised of paired helical filaments of hyperphosphorylated tau. The 39-43 amino acids comprising Aβ peptides are derived from the larger amyloid precursor protein (APP). In the amyloidogenic pathway, Aβ peptides are cleaved from APP by the sequential proteolysis by beta- and gamma-secretases. Aβ peptides are released as soluble proteins and are detected at low level in the cerebrospinal fluid (CSF) in normal aging brain. During the progress of AD the Aβ peptides aggregate and form amyloid deposits in the parenchyma and vasculature of the brain, which can be detected post mortem as diffuse and senile plaques and vascular amyloid during histological examination (for a recent review see: Blennow et al. Lancet. 2006 Jul. 29; 368(9533):387-403).

Alzheimer's disease (AD) is becoming a great health and social economical problem all over the world. There are great efforts to develop techniques and methods for the early detection and effective treatment of the disease. Currently, diagnosis of AD in an academic memory-disorders clinic setting is approximately 85-90% accurate (Petrella J R et al. Radiology. 2003 226:315-36). It is based on the exclusion of a variety of diseases causing similar symptoms and the careful neurological and psychiatric examination, as well as neuropsychological testing.

Molecular imaging has the potential to detect disease progression or therapeutic effectiveness earlier than most conventional methods in the fields of neurology, oncology and cardiology. Among the several promising molecular imaging technologies, such as optical imaging, MRI, SPECT and PET, PET is of particular interest for drug development because of its high sensitivity and ability to provide quantitative and kinetic data.

For example positron emitting isotopes include e.g. carbon, iodine, nitrogen and oxygen. These isotopes can replace their non-radioactive counterparts in target compounds to produce PET tracers that have similar biological properties. Among these isotopes F-18 is a preferred labeling isotope due to its half life of 110 min, which permits the preparation of diagnostic tracers and subsequent study of biochemical processes. In addition, its low β+ energy (634 keV) is also advantageous.

Post-mortem histological examination of the brain is still the only definite diagnosis of Alzheimer's disease. Thus, the in vivo detection of one pathological feature of the disease— the amyloid aggregate deposition in the brain—is thought to have a strong impact on the early detection of AD and differentiating it from other forms of dementia. Additionally, most disease modifying therapies which are in development are aiming at lowering of the amyloid load in the brain. Thus, imaging the amyloid load in the brain may provide an essential tool for patient stratification and treatment monitoring (for a recent review see: Nordberg. Eur J Nucl Med Mol Imaging. 2008 March; 35 Suppl 1:S46-50).

In addition, amyloid deposits are also known to play a role in amyloidoses, in which amyloid proteins (e.g. tau) are abnormally deposited in different organs and/or tissues, causing disease. For a recent review see Chiti et al. Annu Rev Biochem. 2006; 75:333-66.

Fluoropegylated (aryl/heteroaryl vinyl)-phenyl methyl amines such as 4-[(E)-2-(4-{2-[2-(2-fluoroethoxy)ethoxy]ethoxy}phenyl)vinyl]-N-methylaniline and 4-[(E)-2-(6-{2-[2-(2-fluoroethoxy)ethoxy]ethoxy}pyridin-3-yl)vinyl]-N-methylaniline have been labeled with F-18 fluoride and are covered by patent applications WO2006066104, WO2007126733 and members of the corresponding patent families.

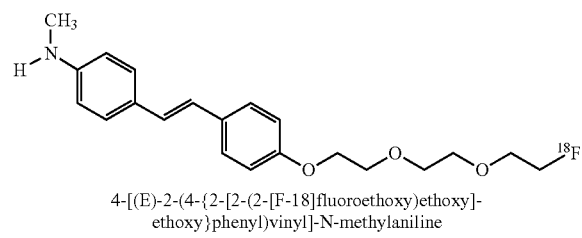

4-[(E)-2-(4-{2-[2-(2-[F-18]fluoroethoxy)ethoxy]ethoxy}phenyl)vinyl]-N-methylaniline 4-[(E)-2-(6-{2-[2-(2-[F-18]fluoroethoxy)ethoxy]ethoxy}pyridin-3-yl)vinyl]-N-methylaniline The usefulness of this radiotracers for the detection of Aβ plaques have been reported in the literature (W. Zhang et al., Nuclear Medicine and Biology 32 (2005) 799-809; C. Rowe et al., Lancet Neurology 7 (2008) 1-7; S. R. Choi et al., The Journal of Nuclear Medicine 50 (2009) 1887-1894).

To not limit the use of such F-18 labeled diagnostics, processes are needed, that allow a robust and safe manufacturing of the F-18 labeled tracers. Additionally, such processes should provide high yield of the overall synthesis to allow the production of quantities of the diagnostic to supply the radiotracer, despite of the half life of 110 min, to facilities without cyclotron or radiopharmaceutical production facility.

Syntheses of F-18 labeled fluoropegylated (aryl/heteroaryl vinyl)-phenyl methyl amines have been described before:

4-[(E)-2-(4-{2-[2-(2-[F-18]fluoroethoxy)ethoxy]ethoxy}phenyl)vinyl]-N-methylaniline 2a -continued

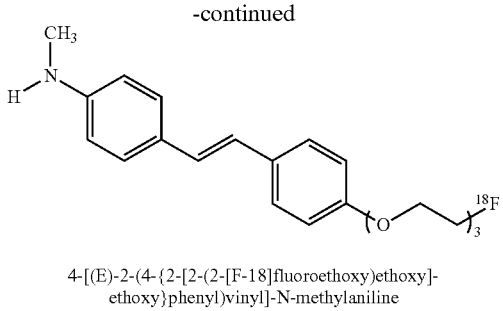

4-[(E)-2-(4-{2-[2-(2-[F-18]fluoroethoxy)ethoxy]-ethoxy}phenyl)vinyl]-N-methylaniline a) W. Zhang et al., Nuclear Medicine and Biology 32 (2005) 799-809

4 mg precursor 2a (2-[2-(2-{4-[(E)-2-{4-[(tert-butoxycarbonyl)(methyl)amino]-phenyl}vinyl]phenoxy}ethoxy)ethoxy]ethyl methanesulfonate) in 0.2 mL DMSO were reacted with [F-18]fluoride/kryptofix/potassium carbonate complex. The intermediate was deprotected with HCl and neutralized with NaOH. The mixture was extracted with ethyl acetate. The solvent was dried and evaporated. The residue was dissolved in acetonitrile and purified by semi-preparative HPLC (acetonitrile/5 mM dimethylglutarate buffer pH 7 9/1). 20% (decay corrected), 11% (not corrected for decay) 4-[(E)-2-(4-{2-[2-(2-[F-18]fluoroethoxy)ethoxy]ethoxy}phenyl)vinyl]-N-methylaniline were obtained within 90 min. An additional re-Formulation, necessary to obtain a solution suitable for injection into human is not described.

b) WO2006066104

4 mg precursor 2a (2-[2-(2-{4-[(E)-2-{4-[(tert-butoxycarbonyl)(methyl)amino]-phenyl}vinyl]phenoxy}ethoxy)ethoxy]ethyl methanesulfonate) in 0.2 mL DMSO were reacted with [F-18]fluoride/kryptofix/potassium carbonate complex. The intermediate was deprotected with HCl and neutralized with NaOH. The mixture was extracted with ethyl acetate. The solvent was dried and evaporated, the residue was dissolved in acetonitrile and purified by semi-preparative HPLC. 30% (decay corrected), 17% (not corrected for decay) 4-[(E)-2-(4-{2-[2-(2-[F-18]fluoroethoxy)ethoxy]ethoxy}phenyl)vinyl]-N-methylaniline were obtained in 90 min. An additional re-Formulation, necessary to obtain a solution suitable for injection into human is not described.

c) C. C. Rowe et al., Lancet Neurology 7 (2008) 129-135

After radiolabeling, acidic hydrolysis and purification by semi-preparative HPLC, 4-[(E)-2-(4-{2-[2-(2-[F-18]fluoroethoxy)ethoxy]ethoxy}phenyl)vinyl]-N-methylaniline was Formulated via solid-phase extraction (SPE).

d) H. Wang et al., Nuclear Medicine and Biology 38 (2011) 121-127

5 mg (9.33 µmol) precursor 2a (2-[2-(2-{4-[(E)-2-{4-[(tert-butoxycarbonyl)(methyl)amino]-phenyl}vinyl]phenoxy}ethoxy)ethoxy]ethyl methanesulfonate) in 0.5 mL DMSO were reacted with [F-18]fluoride/kryptofix/potassium carbonate complex. The intermediate was deprotected with HCl and neutralized with NaOH. The crude product was diluted with acetonitrile/0.1 M ammonium formate (6/4) and purified by semi-preparative HPLC. The product fraction was collected, diluted with water, passed through a C18 cartridge and eluted with ethanol, yielding 17% (not corrected for decay) 4-[(E)-2-(4-{2-[2-(2-[F-18]fluoroethoxy)ethoxy]ethoxy}phenyl)vinyl]-N-methylaniline within 50 min. In the same paper, the conversion of an unprotected mesylate precursor (is described:

5 mg (11.48 µmol) unprotected mesylate precursor (2-{2-[2-(4-{(E)-2-[4-(methylamino)phenyl]vinyl}phenoxy)ethoxy]-ethoxy}ethyl 4-methanesulfonate) in 0.5 mL DMSO were reacted with [F-18]fluoride/kryptofix/potassium carbonate complex. The crude product was diluted with acetonitrile/0.1 M ammonium formate (6/4) and purified by semi-preparative HPLC. The product fraction was collected, diluted with water, passed through a C18 cartridge and eluted with ethanol, yielding 23% (not corrected for decay) 4-[(E)-2-(4-{2-[2-(2-[F-18]fluoroethoxy)ethoxy]ethoxy}phenyl)vinyl]-N-methylaniline within 30 min. A process wherein the radiotracer was purified by SPE (without HPLC) only, was found to afford a product with acceptable radiochemical purity (>95%), however, the chemical purity was too low, e.g. side products derived from the excess of precursor could not be removed.

e) US20100113763

2a (2-[2-(2-{4-[(E)-2-{4-[(tert-butoxycarbonyl)(methyl)amino]phenyl}vinyl]-phenoxy}ethoxy)ethoxy]ethyl methanesulfonate) was reacted with [F-18]fluoride reagent in a mixture of tert-alcohol and acetonitrile. After fluorination, the solvent was evaporated and a mixture of HCl and acetonitrile was added. After deprotection (heating at 100-120° C.), the crude product mixture was purified by HPLC (C18, 60% acetonitrile, 40% 0.1M ammonium formate). An additional re-Formulation, necessary to obtain a solution suitable for injection into human is not described.

4-[(E)-2-(6-{2-[2-(2-(F-18]fluoroethoxy)ethoxy)ethoxy}pyridin-3-yl)vinyl]-N-methylaniline

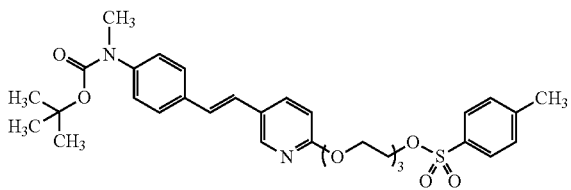

2b

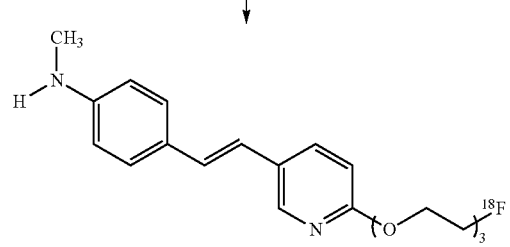

4-[(E)-2-(4-{2-[2-(2-[F-18]fluoroethoxy)ethoxy]-ethoxy}phenyl)pyridin-3-yl]-N-methylaniline a) S. R. Choi et al., The Journal of Nuclear Medicine 50 (2009) 1887-1894.

1 mg precursor 2b (2-{2-[2-({5-[(E)-2-{4-[(tert-butoxycarbonyl)(methyl)amino]-phenyl}vinyl]pyridin-2- yl}oxy)ethoxy]ethoxy}ethyl 4-methylbenzenesulfonate) in 1 mL DMSO was reacted with [F-18] fluoride/kryptofix/potassium carbonate complex. The intermediate was deprotected with HCl and neutralized with NaOH. DMSO and inorganic components were removed by solid-phase-extraction on SepPak light C18 cartridge (Waters). The crude product was purified by semi-preparative HPLC (55% acetonitrile, 45% 20 mM $NH_4OAc$+0.5% w/v sodium ascorbate). The product fraction was diluted with water and passed through a SepPak light C18 cartridge. The radiotracer was eluted with ethanol. The yield for 4-[(E)-2-(6-{2-[2-(2-[F-18]fluoroethoxy)ethoxy]ethoxy}pyridin-3-yl)vinyl]-N-methylaniline was 10-30% (decay corrected).

b) WO2010078370

1.5 mg (2.45 μmol) precursor 2b (2-{2-[2-({5-[(E)-2-{4-[(tert-butoxycarbonyl)(methyl)amino]-phenyl}vinyl]pyridin-2-yl}oxy)ethoxy]ethoxy}ethyl 4-methylbenzenesulfonate) in 2 mL DMSO was reacted with [F-18] fluoride/kryptofix/potassium carbonate complex. The intermediate was deprotected with HCl and diluted with 1% NaOH solution for neutralization. The mixture was loaded onto a reverse phase cartridge. The cartridge was washed with water (containing 5% w/v sodium ascorbate). The crude product was eluted with acetonitrile into a reservoir containing water+5% w/v sodium ascorbate and HPLC solvent. After purification by semi-preparative HPLC, the product fraction was collected into a reservoir containing water+0.5% w/v sodium ascorbate. The solution was passed trough a C18 cartridge, the cartridge was washed with water (containing 0.5% w/v sodium ascorbate and the final product was eluted with ethanol into a vial containing 0.9% sodium chloride solution with 0.5% w/v sodium ascorbate.

c) Y. Liu et al., Nuclear Medicine and Biology 37 (2010) 917-925

1 mg (1.63 μmol) precursor 2b (2-{2-[2-({5-[(E)-2-{4-[(tert-butoxycarbonyl)(methyl)amino]-phenyl}vinyl]pyridin-2-yl}oxy)ethoxy]ethoxy}ethyl 4-methylbenzenesulfonate) in 1 mL DMSO was reacted with [F-18] fluoride/kryptofix/potassium carbonate complex. The intermediate was deprotected with HCl and diluted with 1% NaOH solution. The mixture was loaded onto a Oasis HLB cartridge. The cartridge was washed with water, dried under a flow of argon and the product was eluted with ethanol into a vial containing a saline solution. Although, radiochemical impurities were removed by this procedure, non-radioactive by-products derived from hydrolysis of the excess of precursor, remained in the final product solution.

The yield for 4-[(E)-2-(6-{2-[2-(2-[F-18]fluoroethoxy)ethoxy]ethoxy}pyridin-3-yl)vinyl]-N-methylaniline was 34% (non-decay corrected) within 50 min at a radioactive level from 10-100 mCi (370-3700 MBq) of [F-18]fluoride.

d) L. Silva et al., Abstract/Poster EANM 2010

An IBA Synthera platform was adapted for the synthesis of 4-[(E)-2-(6-{2-[2-(2-[F-18]fluoroethoxy)ethoxy]ethoxy}pyridin-3-yl)vinyl]-N-methylaniline. Additionally, a semi-preparative HPLC system and a further Synthera module for re-Formulation was integrated.

e) G. Casale et al. World Journal of Nuclear Medicine, 9 S1 (2010), S-174 (Abstract of $10^{th}$ Congress of WFNMB, Cape Town, South Africa, 18-23 Sep. 2010)

The manufacturing of 4-[(E)-2-(6-{2-[2-(2-[F-18]fluoroethoxy)ethoxy]ethoxy}pyridin-3-yl)vinyl]-N-methylaniline have been accomplished by use of an IBA Synthera synthesis module, combined with an HPLC semi preparative purification system and an additional module for Formulation (dilution of HPLC fraction, trapping on a C18 cartridge, washing and elution with ethanol).

Although, cartridge based purification processes have been investigated, an optimum of product quality regarding radiochemical purity and separation from non-radioactive by-products have been demonstrated and proofed only for HPLC purification. So far, F-18 labeled fluoropegylated (aryl/heteroaryl vinyl)-phenyl methyl amines have been purified by HPLC using solvent systems consisting of acetonitrile and aqueous buffer. Obviously, collected product fractions can not directly used for administration into patient. Acetonitrile and further compounds of the solvent systems that are not tolerated for injection into human have to be removed. This could be accomplished by evaporation or by solid phase extraction (e.g. trapping on C18 solid phase extracting cartridge and elution with ethanol, see FIG. 1: final solid-phase extraction cartridge C3, elution with ethanol from V8; see also FIG. 7, final solid-phase extraction cartridge 11, elution with ethanol from one of the vials 9).

However, especially at higher levels of radioactivity, decomposition of the radiotracer due to radiolysis processes might be an issue. This problem is well known, to prevent radiolysis during the purification of 4-[(E)-2-(6-{2-[2-(2-[F-18]fluoroethoxy)ethoxy]ethoxy}pyridin-3-yl)vinyl]-N-methylaniline sodium ascorbate (as an radical scavenger) was added to the HPLC solvent and to washing solutions (S. R. Choi et al, WO2010078370). However, the concentration of the radiotracer after HPLC by evaporation or by solid-phase extraction is a critical step of the manufacturing. In upscaling experiments, higher radiochemical purities of F-18 labeled fluoropegylated (aryl/heteroaryl vinyl)-phenyl methyl amines can be found after HPLC, before the solid phase extraction compared to the composition after solid phase extraction.

The general setup of the manufacturing process for F-18 labeled fluoropegylated (aryl/heteroaryl vinyl)-phenyl methyl amines as previously described is illustrated in FIG. 7. The manufacturing process can be divided into three major parts:

A) Synthesis
B) Purification by HPLC
C) Formulation

The manufacturing steps of drying of [F-18]fluoride, radiolabeling of the precursor molecule and deprotection are performed on the part A of the synthesis device (FIG. 7). The crude product mixture is transferred to the second part B for purification by HPLC (on reversed phase silica gel using acetonitrile/buffer eluent). To obtain the radiotracer in a Formulation, suitable for injection into human. The solvent (acetonitrile) present in the product fraction needs to be removed and exchanged by a composition that is appropriate for the manufacturing of a medicament. Typically (and described in the references above), the product fraction is diluted with water (vessel "8", FIG. 7, part C) and then passed through a reversed phase cartridge ("11", FIG. 7, part C). The cartridge is washed with a aqueous solution from one of the reservoirs 9 (FIG. 7, part C) and finally eluted from the cartridge with an ethanolic solution (or ethanol) from another of the reservoirs 9 into the product vial, that optionally comprises further parts and excipients of the final Formulation. It is obvious to those skilled in the art, that the illustration in FIG. 7 is a simplification of process and equipment and that further parts such as valves, vials, tubing ect. can be part of such process or equipment.

A "GMP compliant" manufacturing process for 4-[(E)-2-(6-{2-[2-(2-[F-18]fluoroethoxy)ethoxy]-ethoxy}pyridin-3-yl)vinyl]-N-methylaniline is disclosed in WO2010078370 and C.-H. Yao et al., Applied Radiation and Isotopes 68 (2010) 2293-2297. To prevent the decomposition of 4-[(E)-2-(6-{2-[2-(2-[F-18]fluoroethoxy)ethoxy]-ethoxy}pyridin-3-yl)vinyl]-N-methylaniline, sodium ascorbate was added to the HPLC solvent (45% acetonitrile, 55% 20 mM ammoniumacetate containing 0.5% (w/v) sodium ascorbate) and the final Formulation (0.5% (w/v) sodium ascorbate). The process afforded up to 18.5 GBq (25.4±7.7%, decay corrected) 4-[(E)-2-(6-{2-[2-(2-[F-18]fluoroethoxy)ethoxy]-ethoxy}pyridin-3-yl)vinyl]-N-methylaniline. The radiochemical purity was 95.3±2.2%.

Although ascorbate/ascorbic acid is added to solvents involved in the purification, radiochemical purity was only about 95.3±2.2% at product activity levels of up to 18.5 GBq (Yao et al.)—probably due to decomposition by radiolysis.

At higher product activity levels an even higher variation of radiochemical purity was found for the manufacturing of 4-[(E)-2-(4-{2-[2-(2-[F-18]fluoroethoxy)ethoxy]-ethoxy}phenyl)vinyl]-N-methylaniline (Example 7, FIG. 9, method A).

Beside of the variation of radiochemical purity, the re-Formulation during the current process (conversion of the radiotracer from HPLC media into an injectable solution) requires additional process time and demands more complex equipment. For example, the process for the synthesis of 4-[(E)-2-(6-{2-[2-(2-[F-18]fluoroethoxy)ethoxy] ethoxy}pyridin-3-yl)vinyl]-N-methylaniline described by Silva et al. and Casale et al. demands three modules for the overall manufacturing procedure. The Synthesis of the crude product (schematically illustrated in FIG. 7, Part A) was accomplished on an IBA Synthera module, a semi-preparative HPLC system was used for purification (schematically illustrated in FIG. 7, Part B) and an additional IBA Synthera synthesis module was used for re-Formulation (schematically illustrated in FIG. 7, Part C).

The problem to be solved by the present invention is to provide an improved HPLC purification process for F-18 labeled fluoropegylated (aryl/heteroaryl vinyl)-phenyl methyl amines that provides high chemical and radiochemical purities of the radiotracer, avoiding a concentration of the labeled product after purification to prevent radiolysis, especially at higher levels of radioactivity. Such process should be suitable for the manufacturing of larger quantities (radioactivity) of the radiotracer to allow a distribution to imaging facilities without own radiopharmaceutical production. So far the maximum activity for a F-18 labeled fluoropegylated (aryl/heteroaryl vinyl)-phenyl methyl amine was reported to be 18.5 GBq (Yao et al.). However, even higher yields would be supportive for a widespread use and availability of the radiotracer. A prerequisite of the new manufacturing method should be a high radiochemical purity (e.g. >95%) within a broad range of radioactivity. More precisely, such process should be suitable for the manufacturing of higher activity levels of the radiotracer than previously described (e.g. >20 GBq, or even >50 GBq, or even >100 GBq) with radiochemical purities reliably ≥95%. As an additional feature such process should be less complex than the processes described before.

The problems described above were solved by an modified purification procedure. To simplify the overall setup for manufacturing, the solvent composition for HPLC purification was modified. Instead of an acetonitrile/buffer mixture, an ethanol/buffer mixture is used. An advantage of the new HPLC solvent mixture is, that all constituents of the HPLC solvent—in contrast to previously described compositions—are well tolerated as part of a Formulation, thereby suitable for injection into human. Therefore a re-Formulation to remove constituents of the HPLC solvent (as illustrated in FIG. 7, Part C) is not longer required. This further advantage of the new process—the simplified setup—is schematically illustrated in FIG. 8. (Obviously, this illustration is a simplification that shows a general setup of the new method described herein.) Following the drawing in FIG. 8, the product fraction is collected directly (by switching valve "7") into the product vial (that could contain further parts of the final Formulation). Due to the reduced complexity, the overall manufacturing time by using the new method described herein is shorter, directly contributing to higher non decay corrected yields compared to the previous used process wherein a HPLC purification with additional (time consuming) re-Formulation on a solid-phase cartridge (SPE) is used.

The major advantage of the new method described herein, is the reliably high radiochemical purity of the F-18 labeled fluoropegylated (aryl/heteroaryl vinyl)-phenyl methyl amines synthesized by the new method. In Example 7 and FIG. 9 the radiochemical purity in dependence of purification method and amount (radioactivity) of radiolabeled product at end of synthesis is demonstrated. The dots/squares (each representing an individual experiment) and the trendlines in FIG. 9 clearly demonstrate that the radiochemical purity obtained after HPLC with re-Formulation by SPE varies significantly (FIG. 9, empty squares). Especially at higher radioactivity levels (>20 GBq) the radiochemical purity often is even ≤95%. In contrast, variability of radiochemical purities obtained by the new method of the present invention is much lower and high radiochemical purities of >95% were achieved, even at radioactivity levels of the product of greater than 50 GBq or even greater than 100 GBq (FIG. 9, filled dots).

SUMMARY OF THE INVENTION

The present invention provides a Method for production of radiolabeled compound of Formula I and suitable salts of an inorganic or organic acid thereof, hydrates, complexes, esters, amides, solvates and prodrugs thereof and a optionally a pharmaceutically acceptable carrier, diluent, adjuvant or excipient.

The method comprises the steps of:
Radiofluorination of compound of Formula II
Optionally, cleavage of a protecting group
Purification and Formulation of compound of Formula I by HPLC using a solvent system that can be part of an injectable Formulation

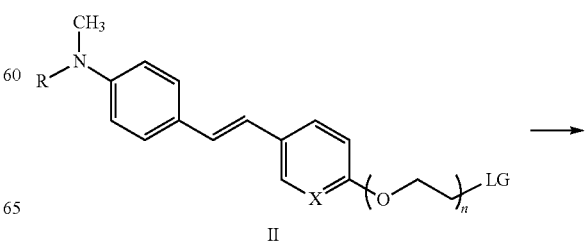

II

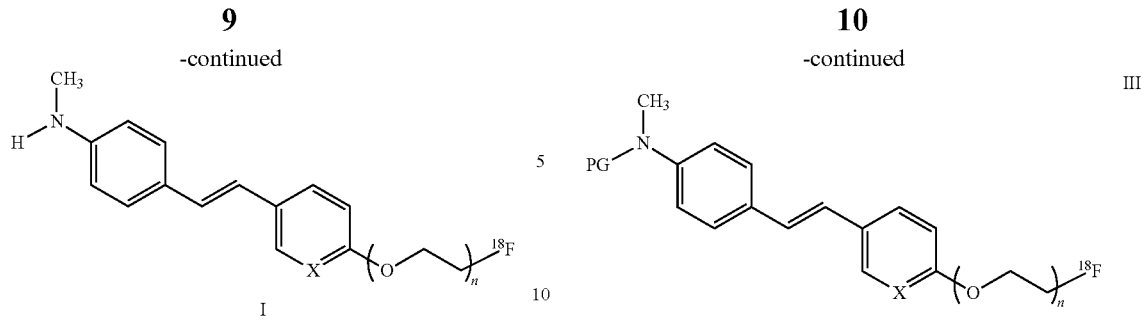

The Method provided by the present invention is schematically illustrated in FIG. 8. Radiofluorination of compound of Formula II and optionally, the cleavage of a protecting group are performed on the left-hand part of the equipment (FIG. 8, part A). The purification of compound of Formula I is performed in a way, that the product fraction obtained by HPLC (FIG. 8, part B) can be directly transferred into the product vial, wherein the product vial optionally contains further pharmaceutically acceptable carriers, diluents, adjuvant or excipients. A further part of process and equipment as illustrated in FIG. 7 (Part C) is not longer required by the Method of the present invention.

The present invention also provides compositions comprising a radiolabeled compound of Formula I or suitable salts of an inorganic or organic acid thereof, hydrates, complexes, esters, amides, solvates and prodrugs thereof and optionally a pharmaceutically acceptable carrier, diluent, adjuvant or excipient.

The present invention also provides a Kit for preparing a radiopharmaceutical preparation by the herein described process, said Kit comprising a sealed vial containing a predetermined quantity of the compound of Formula II.

DESCRIPTION OF THE INVENTION

In a first aspect the present invention is directed to a Method for producing compound of Formula I

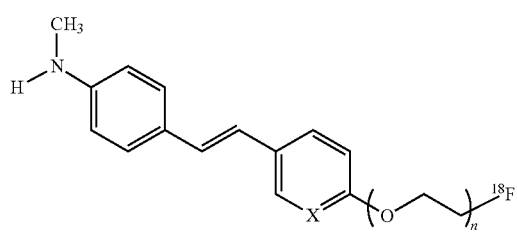

I comprising the steps of:
Step 1: Radiolabeling compound of Formula II with a F-18 fluorinating agent, to obtain compound of Formula I, if R═H or to obtain compound of Formula III, if R═PG

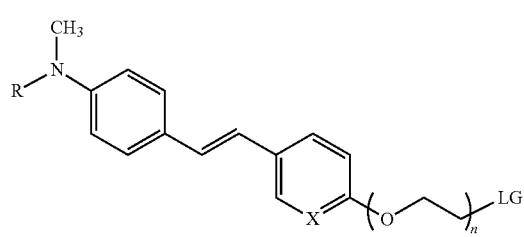

II

Step 2: Optionally, if R═PG, cleavage of the protecting group PG to obtain compound of Formula I Step 3: Purification and Formulation of compound of Formula I wherein:

n=1-6, preferably 2-4, more preferably 3.

X is selected from the group comprising a) CH, b) N.

In one preferred embodiment, X═CH.

In another preferred embodiment, X═N.

R is selected from the group comprising a) H, b) PG.

PG is an "Amine-protecting group".

In a preferred embodiment, PG is selected from the group comprising:

a) Boc, b) Trityl and c) 4-Methoxytrityl.

In a more preferred embodiment, R is H.

In another more preferred embodiment, R is Boc.

LG is a Leaving group.

In a preferred embodiment, LG is selected from the group comprising:

a) Halogen and b) Sulfonyloxy.

Halogen is chloro, bromo or iodo. Preferably, Halogen is bromo or chloro.

In a preferred embodiment Sulfonyloxy is selected from the group consisting of Methanesulfonyloxy, p-Toluenesulfonyloxy, Trifluormethylsulfonyloxy, 4-Cyanophenylsulfonyloxy, 4-Bromophenylsulfonyloxy, 4-Nitrophenylsulfonyloxy, 2-Nitrophenylsulfonyloxy, 4-Isopropylphenylsulfonyloxy, 2,4,6-Triisopropyl-phenylsulfonyloxy, 2,4,6-Trimethylphenylsulfonyloxy, 4-tert-Butyl-phenylsulfonyloxy, 4-Adamantylphenylsulfonyloxy and 4-Methoxyphenylsulfonyloxy.

In a more preferred embodiment, Sulfonyloxy is selected from the group comprising:

a) Methanesulfonyloxy, b) p-Toluenesulfonyloxy, c) (4-Nitrophenyl)sulfonyloxy, d) (4-Bromophenyl)sulfonyloxy.

In a even more preferred embodiment LG is Methanesulfonyloxy.

In another even more preferred embodiment LG is p-Toluenesulfonyloxy.

A preferred compound of Formula I is:

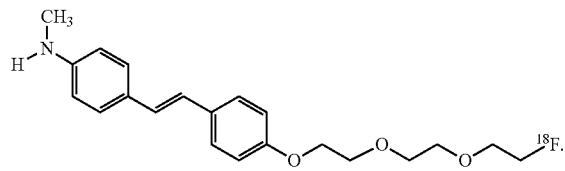

4-[(E)-2-(4-{2-[2-(2-[F-18]fluoroethoxy)ethoxy]ethoxy}phenyl)vinyl]-N-methylaniline.

Another preferred compound of Formula I is:

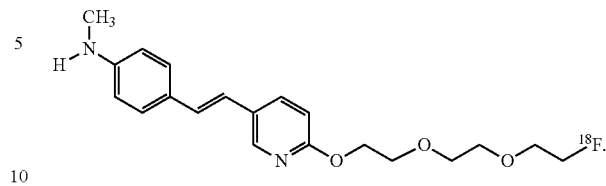

4-[(E)-2-(6-{2-[2-(2-[F-18]fluoroethoxy)ethoxy]ethoxy}pyridin-3-yl)vinyl]-N-methylaniline.

A preferred compound of Formula II is:

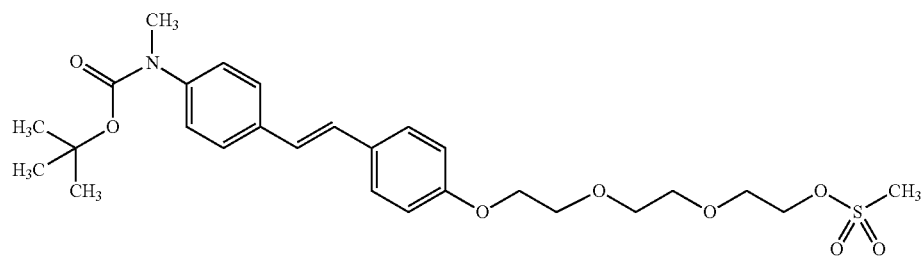 [SMILES: CN(C(=O)OC(C)(C)C)c1ccc(/C=C/c2ccc(OCCOCCOCCOS(C)(=O)=O)cc2)cc1]

2-[2-(2-{4-[(E)-2-{4-[(tert-butoxycarbonyl)(methyl)amino]phenyl}vinyl]phenoxy}-ethoxy)ethoxy]ethyl methanesulfonate.

Another preferred compound of Formula II is:

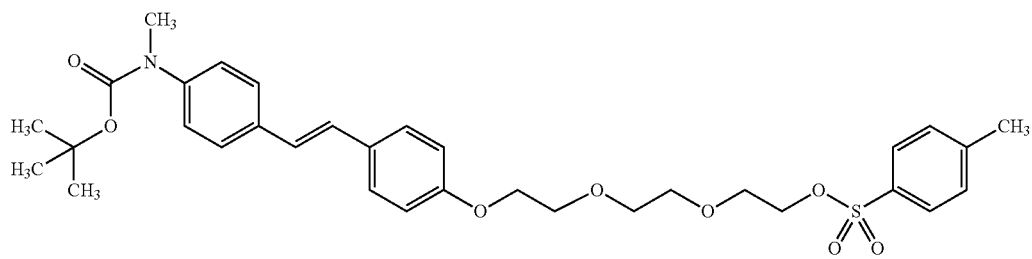 [SMILES: Cc1ccc(S(=O)(=O)OCCOCCOCCOc2ccc(/C=C/c3ccc(N(C)C(=O)OC(C)(C)C)cc3)cc2)cc1]

2-[2-(2-{4-[(E)-2-{4-[(tert-butoxycarbonyl)(methyl)amino]phenyl}vinyl]phenoxy}-ethoxy)ethoxy]ethyl 4-methylbenzenesulfonate Another preferred compound of Formula II is:

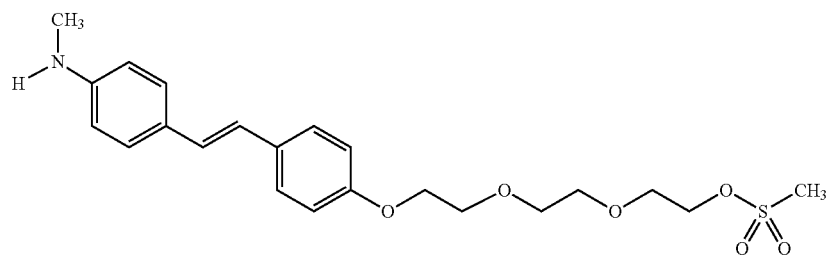 [SMILES: CNc1ccc(/C=C/c2ccc(OCCOCCOCCOS(C)(=O)=O)cc2)cc1]

2-{2-[2-(4-{(E)-2-[4-(methylamino)phenyl]vinyl}phenoxy)ethoxy]ethoxy}ethyl 4-methylbenzenesulfonate Another preferred compound of Formula II is:

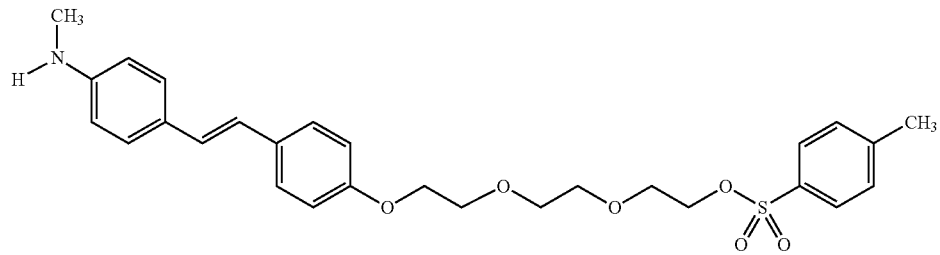 [SMILES: CNc1ccc(/C=C/c2ccc(OCCOCCOCCOS(=O)(=O)c3ccc(C)cc3)cc2)cc1]

2-{2-[2-(4-{(E)-2-[4-(methylamino)phenyl]vinyl}phenoxy)ethoxy]ethoxy}ethyl 4-methylbenzenesulfonate Another preferred compound of Formula II is:

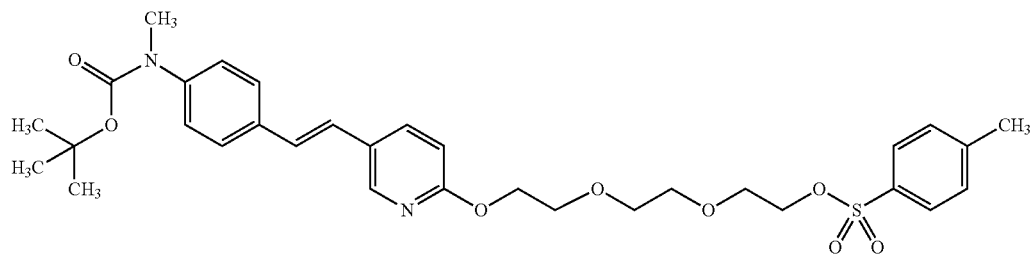 [SMILES: Cc1ccc(S(=O)(=O)OCCOCCOCCOc2ccc(/C=C/c3ccc(N(C)C(=O)OC(C)(C)C)cc3)cn2)cc1]

2-{2-[2-({5-[(E)-2-{4-[(tert-butoxycarbonyl)(methyl)amino]phenyl}vinyl]pyridin-2-yl}oxy)ethoxy]ethoxy}ethyl 4-methylbenzenesulfonate Step 1 comprises a straight forward [F-18]fluoro labeling reaction from compounds of Formula II for obtaining compound of Formula I (if R=H) or compound of Formula III (if R=PG).

The radiolabeling method comprises the step of reacting a compound of Formula II with a F-18 fluorinating agent for obtaining a compound of Formula III or compound of Formula I. In a preferred embodiment, the [F-18]fluoride derivative is 4,7,13,16,21,24-Hexaoxa-1,10-diazabicyclo[8.8.8]-hexacosane K[F-18]F (Kryptofix K[F-18]F), K[F-18]F, H[F-18]F, KH[F-18]F$_2$, Cs[F-18]F, Na[F-18]F or tetraalkylammonium salt of [F-18]F (e.g. [F-18]tetrabutylammonium fluoride). More preferably, the fluorination agent is K[F-18]F, H[F-18]F, [F-18]tetrabutylammonium fluoride, Cs[F-18]F or KH[F-18]F$_2$, most preferably K[F-18], Cs[F-18]F or [F-18]tetrabutylammonium fluoride.

An even more preferred F-18 fluorinating agent is kryptofix/potassium[F-18]fluoride, preferably generated from [F-18]fluoride, kryptofix and potassium carbonate.

The radiofluorination reactions are carried out in acetonitrile, dimethylsulfoxide or dimethylformamide or a mixture thereof. But also other solvents can be used which are well known to someone skilled in the art. Water and/or alcohols can be involved in such a reaction as co-solvent. The radiofluorination reactions are conducted for less than 60 minutes. Preferred reaction times are less than 30 minutes. Further preferred reaction times are less than 15 min. This and other conditions for such radiofluorination are known to experts (Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50).

In one embodiment, 7.5-75 μmol, preferably 10-50 μmol, more preferably 10-30 μmol and even more preferably 12-25 μmol and even more preferably 13-25 μmol of compound of Formula II are used in Step 1.

In another embodiment, more than 7.5 μmol, preferably more than 10 μmol, and more preferable more than 12 μmol and even more preferably more than 13 μmol of compound of Formula II are used in Step 1.

In another embodiment, more than 5 mg, preferably more than 6 mg and more preferably more than 7 mg of compound of Formula II are used in Step 1. In another embodiment 7 mg of compound of Formula II are used in Step 1. In another embodiment 8 mg of compound of Formula II are used in Step 1.

In one preferred embodiment, the Radiofluorination of compound of Formula II is carried out in acetonitrile or in a mixture of acetonitrile and co-solvents, wherein the percentage of acetonitrile is at least 50%, more preferably at least 70%, even more preferably at least 90%.

Optionally, if R=PG, Step 2 comprises the deprotection of compound of Formula III to obtain compound of Formula I. Reaction conditions are known or obvious to someone skilled in the art, which are chosen from but not limited to those described in the textbook Greene and Wuts, Protecting groups in Organic Synthesis, third edition, page 494-653, included herewith by reference. Preferred reaction conditions are addition of an acid and stirring at 0° C.-180° C.; addition of an base and heating at 0° C.-180° C.; or a combination thereof.

Preferably the step 1 and step 2 are performed in the same reaction vessel.

Step 3 comprises the purification and Formulation of compound of Formula I using a HPLC separation system, wherein, the HPLC solvent eluent (e.g. mixtures of ethanol and aqueous buffers) can be part of the injectable Formulation of compound of Formula I. The collected product fraction can be diluted or mixed with other parts of the Formulation.

In a preferred embodiment, the HPLC solvent mixture is consisting of ethanol or an aqueous buffer or an ethanol/aqueous buffer mixture, wherein the aqueous buffer is consisting of components or excipient that can be injected into human. Examples for such aqueous buffer are solutions of sodium chloride, sodium phosphate buffer, ascorbic acid, ascorbate buffer or mixtures thereof.

In a preferred embodiment, the Method for manufacturing of compound of Formula I is carried out by use of a module (review: Krasikowa, Synthesis Modules and Automation in F-18 labeling (2006), in: Schubiger P. A., Friebe M., Lehmann L., (eds), PET-Chemistry—The Driving Force in Molecular Imaging. Springer, Berlin Heidelberg, pp. 289-316) which allows an automated synthesis. More preferably, the Method is carried out by use of an one-pot module. Even more preferable, the Method is carried out on commonly known non-cassette type modules (e.g. Ecker&Ziegler Modular-Lab, GE Tracerlab FX, Raytest SynChrom) and cassette type modules (e.g. GE Tracerlab MX, GE Fastlab, IBA Synthera, Eckert&Ziegler Modular-Lab PharmTracer), optionally, further equipment such as HPLC or dispensing devices are attached to the said modules.

In a second aspect the present invention is directed to a fully automated and/or remote controlled Method for production of compound of Formula I wherein compounds of Formula I, II and III and Steps 1, 2 and 3 are described above. In a preferred embodiment this method is a fully automated process, compliant with GMP guidelines, that provides a Formulation of Formula I for the use of administration (injection) into human.

In a third aspect the present invention is directed to a Kit for the production of a pharmaceutical composition of compound of Formula I.

In one embodiment the Kit comprising a sealed vial containing a predetermined quantity of the compound of Formula II. Preferably, the Kit contains 1.5-75 μmol, preferably 7.5-50 μmol, more preferably 10-50 μmol and even more preferably 12-25 μmol and even more preferably 12-25 μmol and even more preferably 13-25 μmol of compound of Formula II.

In another embodiment the Kit contains more than 7.5 μmol, preferably more than 10 μmol and more preferably more than 12 μmol and even more preferably more than 13 μmol of compound of Formula II.

In another embodiment the Kit contains more than 5 mg, preferably more than 6 mg and more preferably more than 7 mg of compound of Formula II.

In another embodiment the Kit contains 7 mg of compound of Formula II.

In another embodiment the Kit contains 8 mg of compound of Formula II.

The kit also contains a solvent or solvent mixture or the components for the solvent(mixture) for HPLC purification, wherein those solvent, solvent mixture or components are appropriate for the direct use for injection into patient.

Optionally, the Kit contains further components for manufacturing of compound of Formula I, such as solid-phase extraction cartridges, reagent for fluorination (as described above), acetonitrile or acetonitrile and a co-solvent, reagent for cleavage of deprotection group, solvent or solvent mixtures for purification, solvents and excipient for Formulation.

In one embodiment, the Kit contains a platform (e.g. cassette) for a "cassette-type module" (such as Tracerlab MX or IBA Synthera).

DEFINITIONS

In the context of the present invention, preferred salts are pharmaceutically suitable salts of the compounds according to the invention. The invention also comprises salts which for their part are not suitable for pharmaceutical applications, but which can be used, for example, for isolating or purifying the compounds according to the invention.

Pharmaceutically suitable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalene disulphonic acid, acetic acid, trifluoroacetic acid, propionic acid, lactic acid, tartaric acid, malic acid, citric acid, fumaric acid, maleic acid and benzoic acid.

Pharmaceutically suitable salts of the compounds according to the invention also include salts of customary bases, such as, by way of example and by way of preference, alkali metal salts (for example sodium salts and potassium salts), alkaline earth metal salts (for example calcium salts and magnesium salts) and ammonium salts, derived from ammonia or organic amines having 1 to 16 carbon atoms, such as, by way of example and by way of preference, ethylamine, diethylamine, triethylamine, ethyldiisopropylamine, monoethanolamine, diethanolamine, triethanolamine, dicyclohexylamine, dimethylaminoethanol, procaine, dibenzylamine, N methylmorpholine, arginine, lysine, ethylenediamine and N methylpiperidine.

The term Halogen or halo refers to Cl, Br, F or I.

The term "Amine-protecting group" as employed herein by itself or as part of another group is known or obvious to someone skilled in the art, which is chosen from but not limited to a class of protecting groups namely carbamates, amides, imides, N-alkyl amines, N-aryl amines, imines, enamines, boranes, N—P protecting groups, N-sulfenyl, N-sulfonyl and N-silyl, and which is chosen from but not limited to those described in the textbook Greene and Wuts, Protecting groups in Organic Synthesis, third edition, page 494-653, included herewith by reference. The amine-protecting group is preferably Carbobenzyloxy (Cbz), p-Methoxybenzyl carbonyl (Moz or MeOZ), tert-Butyloxycarbonyl (BOC), 9-Fluorenylmethyloxycarbonyl (FMOC), Benzyl (Bn), p-Methoxybenzyl (PMB), 3,4-Dimethoxybenzyl (DMPM), p-methoxyphenyl (PMP) or the protected amino group is a 1,3-dioxo-1,3-dihydro-2H-isoindol-2-yl (phthalimido) or an azido group. The term "Leaving group" as employed herein by itself or as part of another group is known or obvious to someone skilled in the art, and means that an atom or group of atoms is detachable from a chemical substance by a nucleophilic agent. Examples are given e.g.

in Synthesis (1982), p. 85-125, table 2 (p. 86; (the last entry of this table 2 needs to be corrected: "n-$C_4F_9S(O)_2$—O— nonaflat" instead of "n-$C_4H_9S(O)_2$—O— nonaflat"), Carey and Sundberg, Organische Synthese, (1995), page 279-281, table 5.8; or Netscher, Recent Res. Dev. Org. Chem., 2003, 7, 71-83, scheme 1, 2, 10 and 15 and others). (Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50, explicitly: scheme 4 pp. 25, scheme 5 pp 28, table 4 pp 30, FIG. 7 pp 33).

The term Sulfonyloxy refers to —O—$S(O)_2$-Q wherein Q is optionally substituted aryl or optionally substituted alkyl.

The term "alkyl" as employed herein by itself or as part of another group refers to a $C_1$-$C_{10}$ straight chain or branched alkyl group such as, for example methyl, ethyl, propyl, isopropyl, butyl, isobutyl, tert-butyl, pentyl, isopentyl, neopentyl, heptyl, hexyl, decyl or adamantyl. Preferably, alkyl is $C_1$-$C_6$ straight chain or branched alkyl or $C_7$-$C_{10}$ straight chain or branched alkyl. Lower alkyl is a $C_1$-$C_6$ straight chain or branched alkyl.

The term "aryl" as employed herein by itself or as part of another group refers to monocyclic or bicyclic aromatic groups containing from 6 to 10 carbons in the ring portion, such as phenyl, naphthyl or tetrahydronaphthyl.

Whenever the term "substituted" is used, it is meant to indicate that one or more hydrogens on the atom indicated in the expression using "substituted" is/are replaced by one ore multiple moieties from the group comprising halogen, nitro, cyano, trifluoromethyl, alkyl and O-alkyl, provided that the regular valency of the respective atom is not exceeded, and that the substitution results in a chemically stable compound, i. e. a compound that is sufficiently robust to survive isolation to a useful degree of purity from a reaction mixture.

Unless otherwise specified, when referring to the compounds of Formula the present invention per se as well as to any pharmaceutical composition thereof the present invention includes all of the hydrates, salts, and complexes.

The term "F-18" means fluorine isotope $^{18}F$. The term "F-19" means fluorine isotope 19F.

EXAMPLES

Determination of Radiochemical and Chemical Purity

Radiochemical and chemical purities of 4-[(E)-2-(4-{2-[2-(2-[F-18]fluoroethoxy)ethoxy]-ethoxy}phenyl)vinyl]-N-methylaniline and 4-[(E)-2-(4-{2-[2-(2-[F-18]fluoroethoxy)ethoxy]-ethoxy}phenyl)vinyl]-N-methylaniline were determined by analytical HPLC (column: Atlantis T3; 150× 4.6 mm, 3 μm, Waters; solvent A: 5 mM $K_2HPO_4$ pH 2.2; solvent B: acetonitrile; flow: 2 mL/min, gradient: 0:00 min 40% B, 0:00-05:50 min 40-90% B, 05:50-05:60 min 90-40% B, 05:60-09:00 min 40% B).

Retention time of 4-[(E)-2-(4-{2-[2-(2-[F-18]fluoroethoxy)ethoxy]-ethoxy}phenyl)-vinyl]-N-methylaniline: 3.5-3.9 min depending on the HPLC system used for quality control. Due to different equipment (e.g tubing) a difference in retention time is observed between the different HPLC systems. The identity of 4-[(E)-2-(4-{2-[2-(2-[F-18]fluoroethoxy)ethoxy]-ethoxy}phenyl)vinyl]-N-methylaniline was proofed by co-injection with the non-radioactive reference 4-[(E)-2-(4-{2-[2-(2-[F-19]fluoroethoxy)ethoxy]-ethoxy}phenyl)vinyl]-N-methylaniline.

Retention time of 4-[(E)-2-(6-{2-[2-(2-[F-18]fluoroethoxy)ethoxy]-ethoxy}pyridin-3-yl)vinyl]-N-methylaniline: 3.47 min. The identity of 4-[(E)-2-(6-{2-[2-(2-[F-18]fluoroethoxy)ethoxy]-ethoxy}pyridin-3-yl)vinyl]-N-methylaniline was proofed by co-elution with the non-radioactive reference -[(E)-2-(6-{2-[2-(2-[F-19]fluoroethoxy)ethoxy]-ethoxy}pyridin-3-yl)vinyl]-N-methylaniline.

Example 1

Synthesis of 4-[(E)-2-(4-{2-[2-(2-[F-18]fluoroethoxy)ethoxy]-ethoxy}phenyl)vinyl]-N-methylaniline radiosynthesis on Eckert&Ziegler modular lab

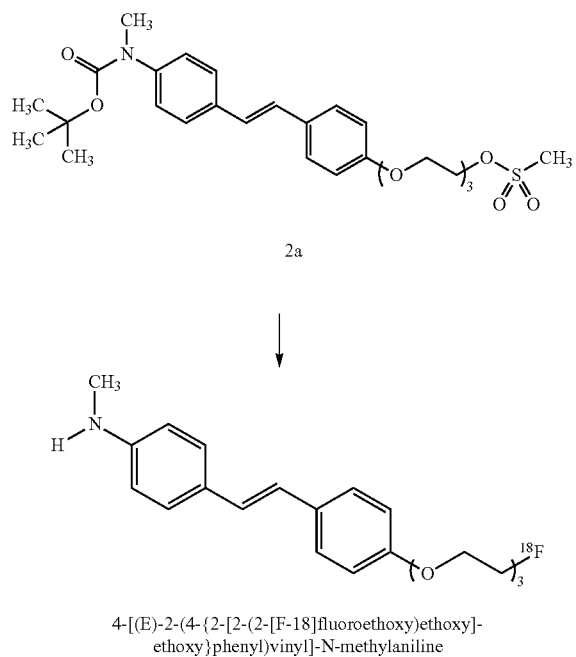

4-[(E)-2-(4-{2-[2-(2-[F-18]fluoroethoxy)ethoxy]-ethoxy}phenyl)vinyl]-N-methylaniline The synthesis of 4-[(E)-2-(4-{2-[2-(2-[F-18])fluoroethoxy)ethoxy]-ethoxy}phenyl)vinyl]-N-methylaniline have been performed on a Eckert&Ziegler modular lab synthesizer. [F-18]Fluoride (60362 MBq) was trapped on a QMA cartridge. The activity was eluted with potassium mesylate/kryptofix/n-$Bu_4NHCO_3$/methanol mixture into the reactor. The solvent was removed while heating under gentle nitrogen stream and vacuum. Drying was repeated after addition of acetonitrile. A solution of 4 mg 2a in 1 mL tert-amylalcohol/acetonitrile (9:1) was added to the dried residue and the mixture was heated for 20 min at 120° C. During heating, the exhaust of the reactor was opened to allow the evaporation of the solvent. A mixture of 2.2 mL 1.5M HCl, 1.1 mL acetonitrile and 30 mg sodium ascorbate was added and the reactor was heated at 100° C. for 10 min. The crude product was neutralized (1.5 mL 2M NaOH+0.3 mL buffer) and transferred to a semi-preparative HPLC column (Synergy Hydro-RP, 250×10 mm, Phenomenex). A mixture of 60% ethanol and 40% ascorbate buffer (pH 7.0) was flushed through the column with 3 mL/min. The product fraction at ≈18 min (FIG. 2) was directly collected into the product vial containing 8.5 mL Formulation basis (phosphate buffer, ascorbic acid, PEG400). Analytical HPLC of the final product (FIG. 3) showed excellent radiochemical and chemical purity. Only cold 4-[(E)-2-(4-{2-[2-(2-[F-18]fluoroethoxy)ethoxy]-ethoxy}phenyl)vinyl]-N-methylaniline have been detected in the UV chromatogram (FIG. 3, bottom), all non-radioactive impurities have been separated. The radiochemical purity was determined to be 99.6%.

Example 2

Synthesis of 4-[(E)-2-(4-{2-[2-(2-[F-18]fluoroethoxy)ethoxy]-ethoxy}phenyl)vinyl]-N-methylaniline radiosynthesis on Tracerlab $FX_N$ A Tracerlab $FX_N$ synthesizer have been adopted to the "direct cut HPLC approach" (FIG. 4).

[F-18]Fluoride (3700 MBq) was trapped on a QMA cartridge. The activity was eluted with potassium carbonate/kryptofix/acetonitrile/water mixture into the reactor. The solvent was removed while heating under gentle nitrogen stream and vacuum. Drying was repeated after addition of acetonitrile. A solution of 7 mg 2a in 1 mL acetonitrile was added to the dried residue and the mixture was heated for 8 min at 120° C. After cooling to 60° C., a mixture of 0.5 mL 2M HCl, and 0.5 mL acetonitrile was added and the reactor was heated at 110° C. for 4 min. The crude product was neutralized (1 mL 1M NaOH+2 mL buffer) and transferred to a semi-preparative HPLC column (Synergy Hydro-RP, 250×10 mm, Phenomenex). A mixture of 60% ethanol and 40% ascorbate buffer (pH 7.0) was flushed through the column with 3 mL/min. The product fraction at ≠16 min (FIG. 2) was directly collected into the product vial containing 8.5 Formulation basis (phosphate buffer, ascorbic acid, PEG400). Radiochemical purity was determined to be >99%.

Example 3

Synthesis of 4-[(E)-2-(4-{2-[2-(2-[F-18]fluoroethoxy)ethoxy]-ethoxy}phenyl)vinyl]-N-methylaniline radiosynthesis on Tracerlab MX and Eckert&Ziegler Purification unit A Kit have been assembled for the synthesis of 4-[(E)-2-(4-{2-[2-(2-[F-18]fluoroethoxy)ethoxy]-ethoxy}phenyl)vinyl]-N-methylaniline (Table 1).

TABLE 1

Composition of Kit for manufacturing of 4-[(E)-2-(4-{2-[2-(2-[F-18]fluoroethoxy)ethoxy]-ethoxy}phenyl)vinyl]-N-methylaniline on tracerlab MX and Eckert&Ziegler Purification unit

| | |
|---|---|
| Eluent vial | 22 mg kryptofix. 7 mg potassium carbonate in 300 μL water + 300 μL acetonitrile |
| Blue capped vial | 8 mL acetonitrile |
| Red capped vial | 8 mg precursor 2a |
| Green capped vial | 2 mL 1.5M HCl + 30 mg sodium ascorbate |
| 2 mL syringe | 1.5 mL 2M NaOH + 0.3 mL phosphate buffer |
| Water bag | Water |
| Product line to Eckert&Ziegler purification unit | Tube with two luer lock fittings |
| Anion exchange cartridge | QMA light, Waters (pre-conditioned) |
| Disposable 3-way valve | With tubing and needle to product vial, incl. sterile filters |

TABLE 1-continued

Composition of Kit for manufacturing of 4-[(E)-2-(4-{2-[2-(2-[F-18]fluoroethoxy)ethoxy]-ethoxy}phenyl)vinyl]-N-methylaniline on tracerlab MX and Eckert&Ziegler Purification unit

| | |
|---|---|
| Product vial | 20 mL vial |
| Formulation basis | 8.5 mL (PEG 400, $Na_2HPO_4 \cdot H_2O$, ascorbic acid in water) |
| HPLC solvent | ethanol |
| | water |
| | sodium ascorbate |
| | ascorbic acid |
| HPLC flow rate | 3 mL/min |

The design of the Tracerlab MX cassette has been adopted (FIG. 5). [F-18]Fluoride was trapped on the QMA cartridge. The activity was eluted with potassium carbonate/kryptofix/acetonitrile/water mixture (from "eluent vial") into the reactor. The solvent was removed while heating under gentle nitrogen stream and vacuum. Drying was repeated after addition of acetonitrile. A solution of 8 mg 2a in 1.8 mL acetonitrile (acetonitrile from "blue capped vial" was added to solid 2a in the "red capped vial" during the sequence) was added to the dried residue and the mixture was heated for 10 min at 120° C. 1.5M HCl (from "green capped vial") was added and the reactor was heated at 110° C. for 5 min. The crude product was neutralized (1 mL 1M NaOH+0.3 mL buffer, from "2 mL syringe") and transferred to the injection valve of the Eckert&Ziegler HPLC (FIG. 6) by the left syringe pump of the MX module. The crude product was purified on a Synergy Hydro-RP, 250×10 mm, Phenomenex HPLC column using a mixture of 60% ethanol and 40% ascorbate buffer (pH 7.0). The product fraction at ≈17.5 min (FIG. 2) was directly collected into the product vial containing 8.5 Formulation basis (phosphate buffer, ascorbic acid, PEG400).

Example 4

Synthesis of 4-[(E)-2-(4-{2-[2-(2-[F-18]fluoroethoxy)ethoxy]-ethoxy}phenyl)vinyl]-N-methylaniline radiosynthesis on Eckert&Ziegler modular lab The synthesis has been performed on Eckert & Ziegler ModularLab synthesizer using acetonitrile as solvent for fluorination. The setup of the synthesizer and the results are summarized in Table 2.

[F-18]Fluoride was trapped on a QMA cartridge (C1). The activity was eluted with a kryptofix mixture (from "V1") into the reactor. The solvent was removed while heating under gentle nitrogen stream and vacuum. Drying was repeated after addition of 100 μL acetonitrile (from "V2"). The solution of precursor 2a (from "V3") was added to the dried residue and the mixture was heated for 10 min at 120° C. After cooling to 40° C., 2 mL 1.5M HCl (from "V4") was added and solution was heated for 5 min at 110° C.

The crude product mixture was diluted with 1.2 mL 2M NaOH and 0.8 mL ammonium formate (1 M) from vial "V5" and then transferred to the HPLC vial ("Mix-Vial") containing previously 1 mL acetonitrile and 0.5 mL ethanol.

The mixture was transferred to the 10 mL sample injection loop of the semi-preparative HPLC using a nitrogen overpressure in the HPLC vial ("Mix-Vial") and via a liquid sensor which controlled the end of the loading. The mixture is loaded to the semi-preparative HPLC column (Synergi Hydro-RP, 250×10 mm, Phenomenex). A mixture of 60% ethanol and 40% ascorbate buffer was flushed through the column with 6 mL/min. The product fraction at ≈7 min was collected directly into the product vial containing 15 mL Formulation basis (consisting of phosphate buffer, PEG400 and ascorbic acid). Analytical HPLC of the final product showed excellent radiochemical and chemical purity. No impurity higher than 0.3 µg/mL was quantified.

TABLE 2

| | |
|---|---|
| Vial V1 | 22 mg kryptofix |
| | 7 mg potassium carbonate |
| | 300 µL acetonitrile |
| | 300 µL water |
| Vial V2 | 100 µL acetonitrile |
| Vial V3 | 8 mg precursor 2a in 1.8 mL acetonitrile |
| Vial V4 | 2 mL HCl 1.5M |
| Vial V5 | 1.2 mL NaOH 2.0M |
| | 800 µL ammonium formate 1M |
| Cartridge C1 | QMA light (waters) conditioned with potassium carbonate 0.5M |
| Mix-Vial | 1 mL acetonitrile |
| | 500 µL ethanol |
| HPLC column | Synergi Hydro-RP, 250*10 mm, 10 µm 80Å, Phenomenex |
| HPLC solvent | 60% ethanol, 40% ascorbate buffer (5 g/l sodium ascorbate and 50 mg/l ascorbic acid) |
| HPLC flow | 6 mL/min |
| Start activity of [F-18]fluoride | 46.0 GBq |
| Product activity | 19.4 GBq |
| Product radio-purity (RCP) | 99% |
| Radiochemical yield | 42% (not corrected for decay) |

Example 5

Synthesis of 4-[(E)-2-(4-{2-[2-(2-[F-18]fluoroethoxy)ethoxy]-ethoxy}phenyl)vinyl]-N-methylaniline radiosynthesis on tracerlab MX and Eckert&Ziegler Purification Unit The synthesis has been performed on GE TracerLab MX synthesizer, purification of 4 has been performed on Eckert & Ziegler Purification Unit. The filling of the injection loop of the HPLC was controlled using the syringe of the MX module. The setup of both automates and the results are summarized in the Table below. [F-18]Fluoride was trapped on a QMA cartridge (C1). The activity was eluted with a kryptofix mixture (from "V1") into the reactor. The solvent was removed while heating under gentle nitrogen stream and vacuum. Drying was repeated after addition of acetonitrile (from "V2"). The solution of precursor 2a (from "V3") was added to the dried residue and the mixture was heated for 10 min at 120° C. After cooling to 40° C., 2 mL 1.5M HCl (from "V4") was added and solution was heated for 5 min at 110° C.

The crude product mixture was diluted with 1.2 mL 2M NaOH and 0.8 mL ammonium formate (1 M) from syringe "S1" and then transferred to the HPLC vial ("Mix-Vial") in which 1 mL acetonitrile (from "V2") and 0.5 mL ethanol (from "V5") are added separately.

The average 6-7 mL mixture was transferred to a 30 mL syringe which then pushed the totality of the volume into the 10 mL sample injection loop of the semi-preparative HPLC. The mixture is loaded to the semi-preparative HPLC column (Synergi Hydro-RP, 250×10 mm, Phenomenex). A mixture of 60% ethanol and 40% ascorbate buffer was flushed through the column with 6 mL/min. The product fraction at ≈9 min was collected for 50 sec directly into the product vial containing 15 mL Formulation basis (consisting of phosphate buffer, PEG400 and ascorbic acid). Analytical HPLC of the final product showed excellent radiochemical and chemical purity. No impurity higher than 0.5 µg/mL was quantified.

TABLE 3

| | |
|---|---|
| Vial V1 | 22 mg kryptofix |
| | 7 mg potassium carbonate |
| | 300 µL acetonitrile |
| | 300 µL water |
| Vial V2 | 8 mL acetonitrile |
| Vial V3 | 8 mg precursor in 1.8 mL acetonitrile |
| Vial V4 | 2 mL HCl 1.5M |
| Vial V5 | 8 mL ethanol |
| Syringe S1 | 1.2 mL NaOH 2.0M |
| | 800 µL ammonium formate 1M |
| Cartridge C1 | QMA light (waters) conditioned with potassium carbonate 0.5M |
| HPLC column | Synergi Hydro-RP, 250* × 10 mm, 10 µm 80Å, Phenomenex |
| HPLC solvent | 60% ethanol, 40% ascorbate buffer (5g/l sodium ascorbate and 50 mg/l ascorbic acid) |
| HPLC flow | 6 mL/min |
| Start activity of [F-18]fluoride | 36.9 GBq |
| Product activity | 14.2 GBq |
| Product radio-purity (RCP) | 100% |
| Radiochemical yield | 38% (not corrected for decay) |

Example 6

Synthesis of 4-[(E)-2-(4-{2-[2-(2-[F-18]fluoroethoxy)ethoxy]-ethoxy}phenyl)vinyl]-N-methylaniline radiosynthesis on tracerlab MX and Eckert&Ziegler Purification Unit The synthesis has been performed on GE TracerLab MX synthesizer, purification of 4 has been performed on Eckert & Ziegler Purification Unit. The filling of the injection loop of the HPLC was controlled by a fluid detector of the Eckert&Ziegler Purification unit. The setup of both automates and the results are summarized in the Table below. [F-18]Fluoride was trapped on a QMA cartridge (C1). The activity was eluted with a kryptofix mixture (from "V1") into the reactor. The solvent was removed while heating under gentle nitrogen stream and vacuum. Drying was repeated after addition of acetonitrile (from "V2"). The solution of precursor (from "V3") was added to the dried residue and the mixture was heated for 10 min at 120° C. After cooling to 40° C., 2 mL 1.5M HCl (from "V4") was added and solution was heated for 5 min at 110° C.

The crude product mixture was diluted with 1.2 mL 2M NaOH and 0.8 mL ammonium formate (1 M) from syringe "S1". 1 mL acetonitrile (from "V2") and 0.5 mL ethanol (from "V5") are added separately to the mixture and then transferred to the right syringe of the GE TracerLab MX automate.

The mixture was transferred to the 10 mL sample injection loop of the semi-preparative HPLC using the right syringe of the GE TracerLab MX automate via a liquid sensor which controlled the end of the loading. The mixture was loaded to the semi-preparative HPLC column (Synergi Hydro-RP, 250×10 mm, Phenomenex). A mixture of 60% ethanol and 40% ascorbate buffer was flushed through the column with 6 mL/min. The product fraction at ≈9 min was collected directly during 50 sec into the product vial containing 15 mL Formulation basis (consisting of phosphate buffer, PEG400 and ascorbic acid). Analytical HPLC of the final product showed excellent radiochemical and chemical purity. No impurity higher than 0.7 µg/mL was quantified.

TABLE 4

| | |
|---|---|
| Vial V1 | 22 mg kryptofix |
| | 7 mg potassium carbonate |
| | 300 µL acetonitrile |
| | 300 µL water |
| Vial V2 | 8 mL acetonitrile |
| Vial V3 | 8 mg precursor in 1.8 mL acetonitrile |
| Vial V4 | 2 mL HCl 1.5M |
| Vial V5 | 8 mL ethanol |
| Syringe S1 | 1.2 mL NaOH 2.0M |
| | 800 µL ammonium formate 1M |
| Cartridge C1 | QMA light (waters) conditioned with potassium carbonate 0.5M |
| HPLC column | Synergi Hydro-RP, 250* × 10 mm, 10 µm 80Å, Phenomenex |
| HPLC solvent | 60% ethanol, 40% ascorbate buffer (5 g/l sodium ascorbate and 50 mg/l ascorbic acid) |
| HPLC flow | 6 mL/min |
| Start activity of [F-18]fluoride | 62.2 GBq |
| Product activity | 24.8 GBq |
| Product radio-purity (RCP) | 100% |
| Radiochemical yield | 40% (not corrected for decay) |

Example 7

Influence of Purification Method on Radiochemical Purity

A series of 4-[(E)-2-(4-{2-[2-(2-[F-18]fluoroethoxy)ethoxy]-ethoxy}phenyl)vinyl]-N-methylaniline syntheses was performed on two different synthesizers (Eckert & Ziegler modular lab and GE tracerlab MX) as generally described in the examples 1, 3-6. The radiolabelings have been performed using 4-10 mg precursor 2a in acetonitrile as well as in tert-amylalcohol/acetonitrile mixture at 100-120° C. for 10-20 min. (in case of radiolabelings in tert-amylalcohol the solvent was evaporated prior deprotection). The N-Boc protecting group was removed by heating with HCl (1.5M-2M).

Crude product mixtures were individually purified by one of the two methods A) or B).
Method A):

The crude product mixture obtained after deprotection is neutralized with a mixture of 2M NaOH and 0.1M ammonium formate and injected onto a semipreparative HPLC (e.g. column: Gemini C18, 10×250 mm, 5 µm, Phenomenex; solvent: 70% acetonitrile, 30% ammonium formate buffer 0.1M with 5 mg/mL sodium ascorbate, flow rate 3 mL/min). The product fraction is collected into a flask containing approx. 160 mL water with 10 mg/mL sodium ascorbate. The mixture is passed through a C18 cartridge (tC18 SepPak environmental, Waters). The cartridge is washed with approx. 8-10 mL 20% EtOH in water (containing 10 mg/mL sodium ascorbate). Finally, the product is eluted with 1.5 to 3 mL ethanol into a vial containing 8.5 to 17 mL "Formulation basis" (comprising PEG400, phosphate buffer and ascorbic acid).
Method B):

The crude product mixture obtained after deprotection is neutralized with a mixture of 2M NaOH and 0.1M ammonium formate and injected onto a semipreparative HPLC (column: e.g.: Gemini C18, 10×250 mm, 5 µm, Phenomenex or Synergi Hydro-RP, 250×10 mm, 10 µm 80 Å, Phenomenex or Synergi Hydro-RP, 250×10 mm, 4 µm 80 Å, Phenomenex; solvent: 60-70% ethanol, 40-30% ascorbate buffer ≈5 mg/mL ascorbate; flow 3 mL/min or 4 mL/min or 6 mL/min). The product fraction is directly collected into a vial containing "Formulation basis" (comprising PEG400, phosphate buffer and ascorbic acid) to provide 10-24 mL of the final Formulation. The peak-cutting time was adjusted in the software to obtain a Formulation comprising 15% EtOH.

Every empty square (each one result for a synthesis comprising a purification by method A, 110 experiments) and every filled dot (each one result for a synthesis comprising a purification by method B, 105 experiments) in FIG. 9 represents an individual experiment for the manufacturing of 4-[(E)-2-(4-{2-[2-(2-[F-18]fluoroethoxy)ethoxy]-ethoxy}phenyl)vinyl]-N-methylaniline. The tendency of radiochemical purity in correlation with radioactivity of the final product is illustrated by linear trendlines.

The radiochemical purity obtained after HPLC with re-Formulation by SPE (method A) varies significantly (FIG. 9, empty squares). Especially at higher radioactive levels (>20 GBq) the radiochemical purity often is even ≤95%.

In contrast, variability is much lower for method B). Consistently high radiochemical purities of >95% were achieved at activity levels of the product of greater than 50 GBq, and even greater than 100 GBq (FIG. 9, filled dots).

Example 8

Synthesis of 4-[(E)-2-(6-{2-[2-(2-[F-18]fluoroethoxy)ethoxy]-ethoxy}pyridin-3-yl)vinyl]-N-methylaniline on Tracerlab FX$_N$

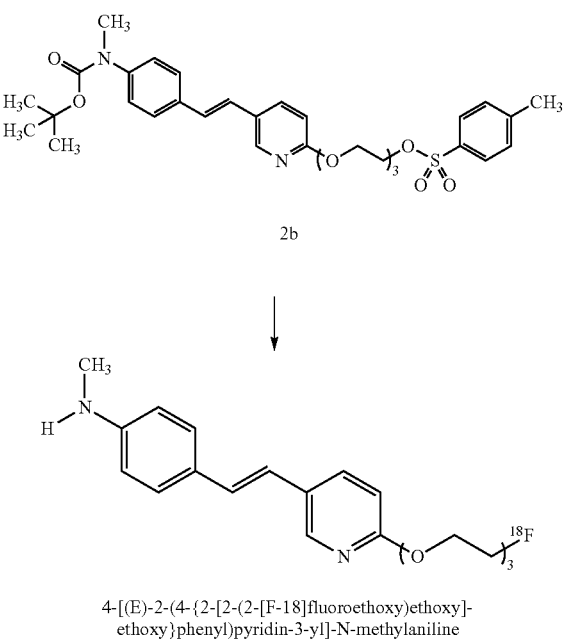

4-[(E)-2-(4-{2-[2-(2-[F-18]fluoroethoxy)ethoxy]-ethoxy}phenyl)pyridin-3-yl]-N-methylaniline A Tracerlab FX$_N$ synthesizer has been adopted to the "direct cut HPLC approach" (FIG. 4).

[F-18]Fluoride (10 GBq) was trapped on a QMA cartridge. The activity was eluted with potassium carbonate/ kryptofix/acetonitrile/water mixture into the reactor. The solvent was removed while heating under gentle nitrogen stream and vacuum. Drying was repeated after addition of acetonitrile. A solution of 8 mg 2b in 1.5 mL acetonitrile was added to the dried residue and the mixture was heated for 10 min at 120° C. After cooling to 60° C., 1 mL 1.5M HCl was added and the reactor was heated at 110° C. for 5 min. The crude product was neutralized (1 mL 1M NaOH/ammonium formate), diluted (with 0.5 mL EtOH and 1.5 mL MeCN) and transferred to a semi-preparative HPLC column (Synergy Hydro-RP, 250×10 mm, Phenomenex). A mixture of 60% ethanol and 40% ascorbate buffer (5 g/l sodium ascorbate and 50 mg/l ascorbic acid, pH 7.0) was flushed through the column with 3 mL/min. The product fraction at ≈10 min (see FIG. 10) was directly collected for 100 sec and mixed with 15 mL Formulation basis (phosphate buffer, ascorbic acid, PEG400).

4.2 GBq (42% not corrected for decay) were obtained in 61 min overall synthesis time. Radiochemical purity (determined by HPLC, $t_R$=3.42 min) was determined to be >99%.

Example 9

Synthesis of 4-[(E)-2-(4-{2-[2-(2-[F-18]fluoroethoxy)ethoxy]-ethoxy}phenyl)vinyl]-N-methylaniline on Tracerlab FX$_N$

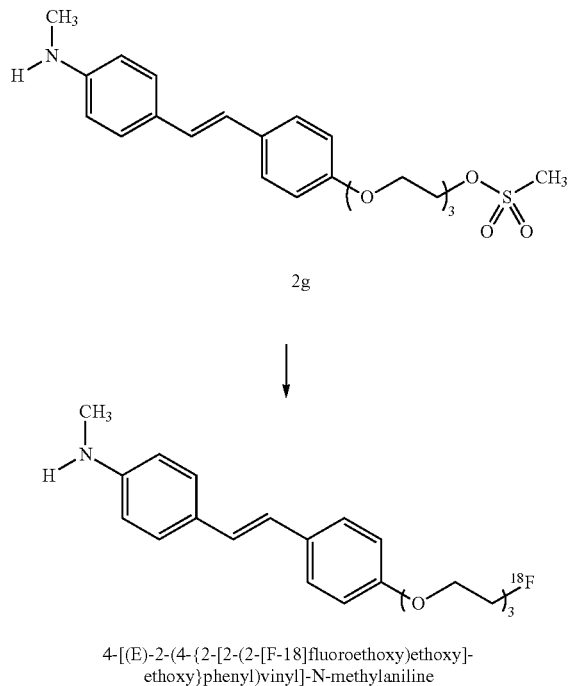

4-[(E)-2-(4-{2-[2-(2-[F-18]fluoroethoxy)ethoxy]-ethoxy}phenyl)vinyl]-N-methylaniline A Tracerlab FX$_N$ synthesizer have been adopted to the "direct cut HPLC approach" (FIG. 4).

[F-18]Fluoride (6.85 GBq) was trapped on a QMA cartridge. The activity was eluted with potassium carbonate/kryptofix/acetonitrile/water mixture into the reactor. The solvent was removed while heating under gentle nitrogen stream and vacuum. Drying was repeated after addition of acetonitrile. A solution of 8 mg 2c in 1.5 mL acetonitrile was added to the dried residue and the mixture was heated for 10 min at 120° C. After cooling to 60° C., the crude product was diluted with 4 mL HPLC eluent and transferred to a semi-preparative HPLC column (Synergy Hydro-RP, 250×10 mm, Phenomenex). A mixture of 60% ethanol and 40% ascorbate buffer (5 g/l sodium ascorbate and 50 mg/l ascorbic acid, pH 7.0) was flushed through the column with 3 mL/min. The product fraction at ≈12 min was directly collected for 100 sec and mixed with 15 mL Formulation basis (phosphate buffer, ascorbic acid, PEG400).

2.54 GBq (37% not corrected for decay) were obtained in 53 min overall synthesis time. Radiochemical purity (determined by HPLC, $t_R$=3.78 min) was determined to be >99%.

Figure 1:
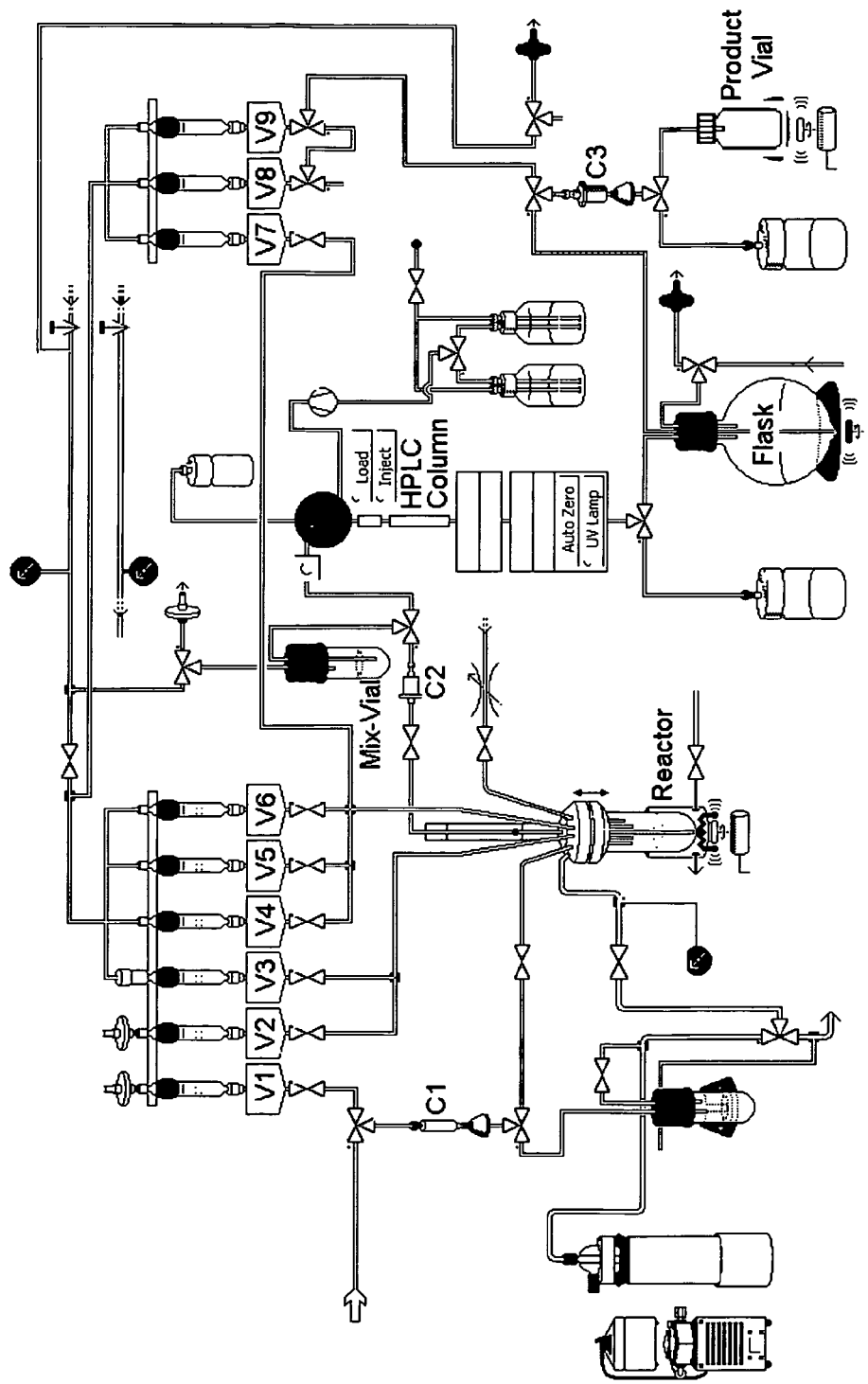
FIG. 1 Setup of Tracerlab FX$_N$ for purification with re-Formulation (adopted from tracerlab software)
Figure 2:
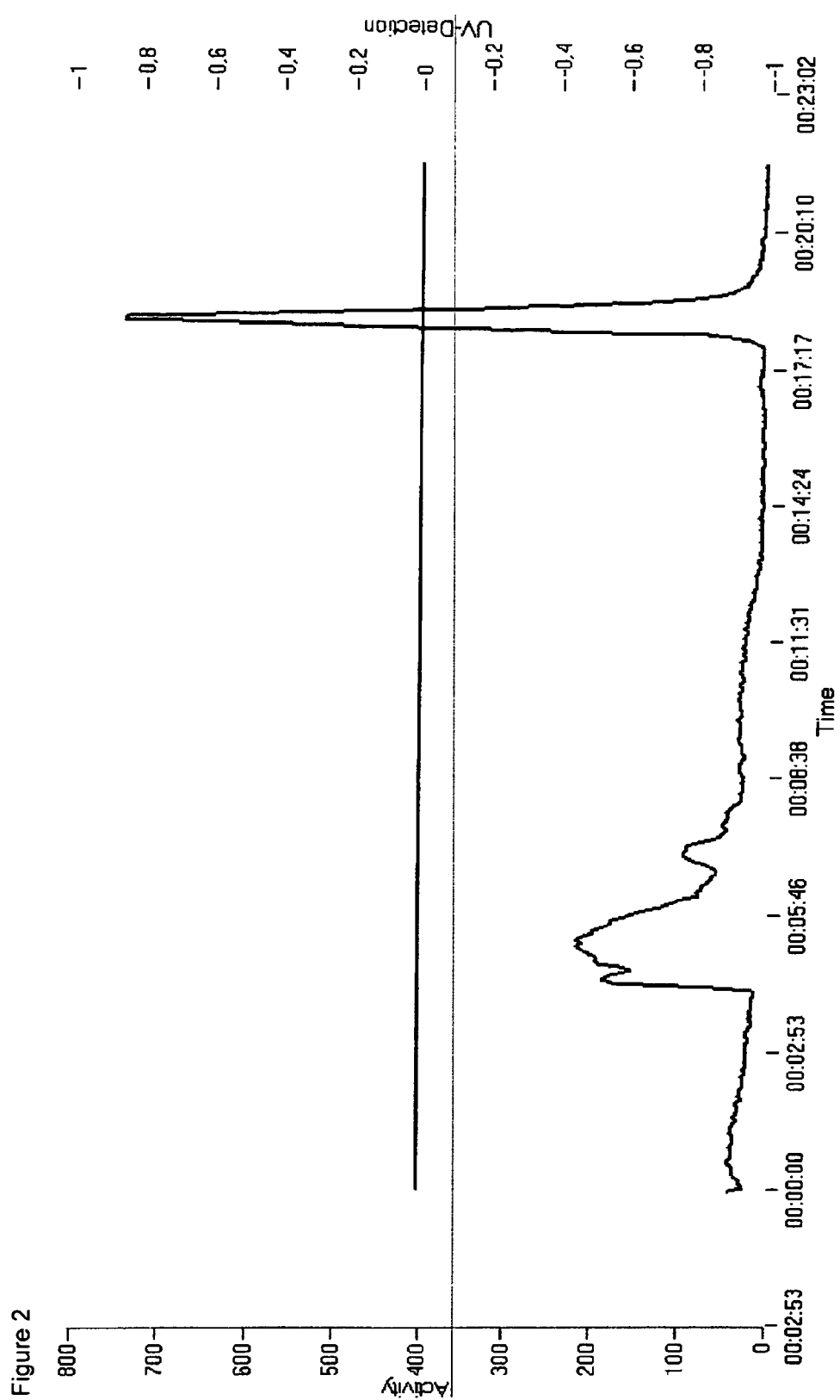
FIG. 2 Chromatogramm of purification using Synergy column on Eckert&Ziegler modular lab (Radioactivity channel)
Figure 3:
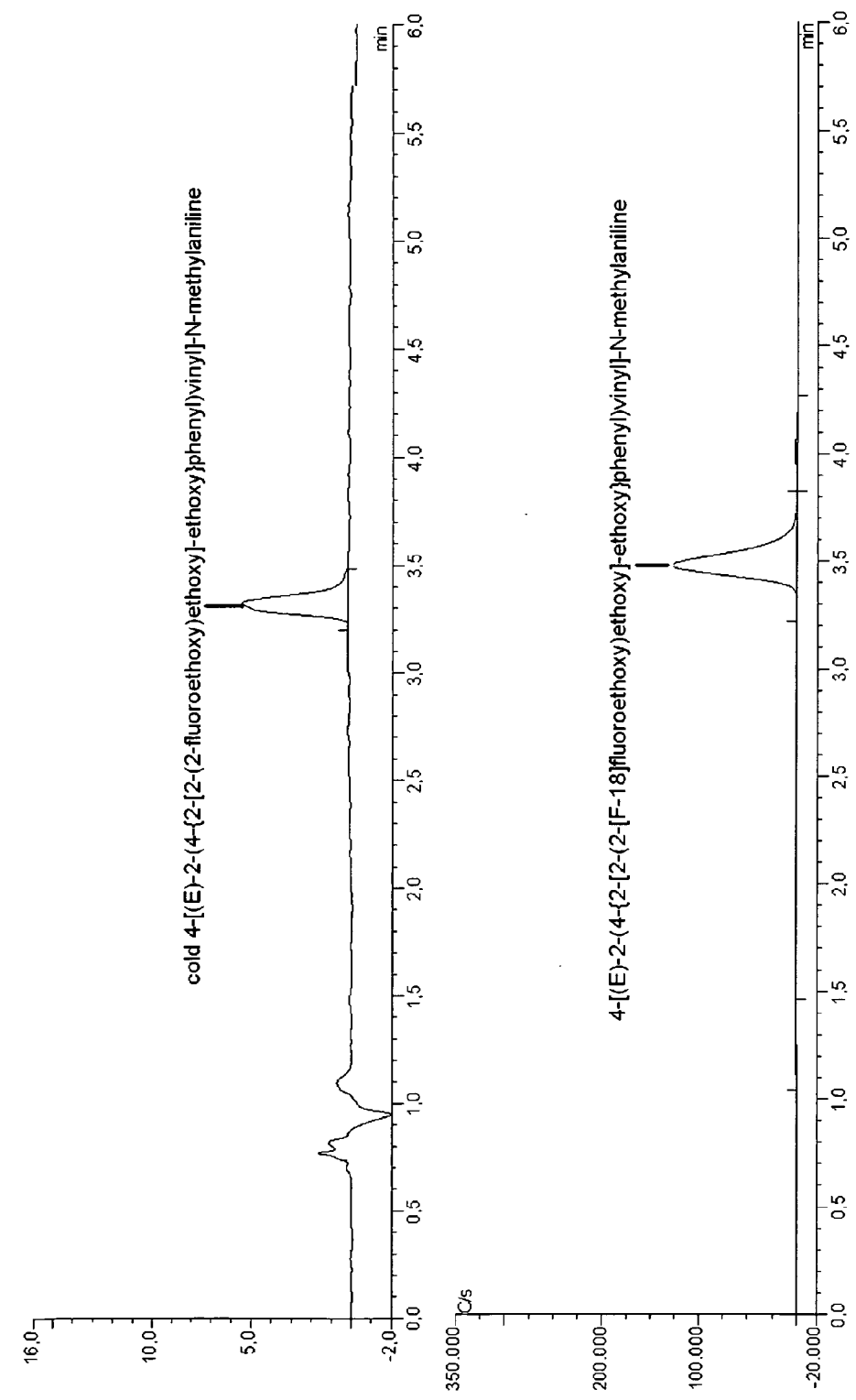
FIG. 3 Analytical HPLC of radiolabeled product (top radioactivity channel, bottom UV channel)
Figure 4:
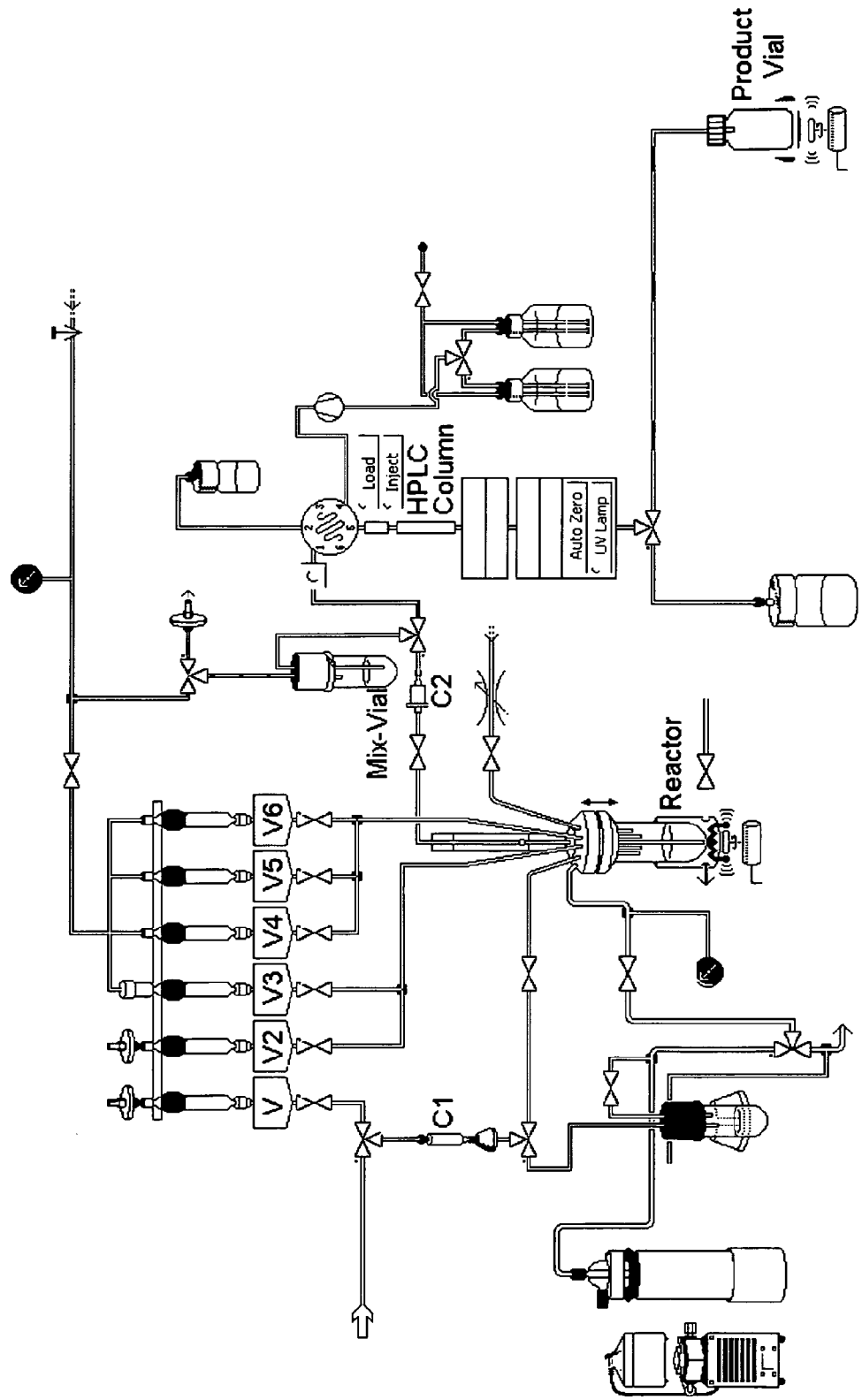
FIG. 4 Setup of Tracerlab FX$_N$ for purification without re-Formulation (adopted from tracerlab software)
Figure 5:
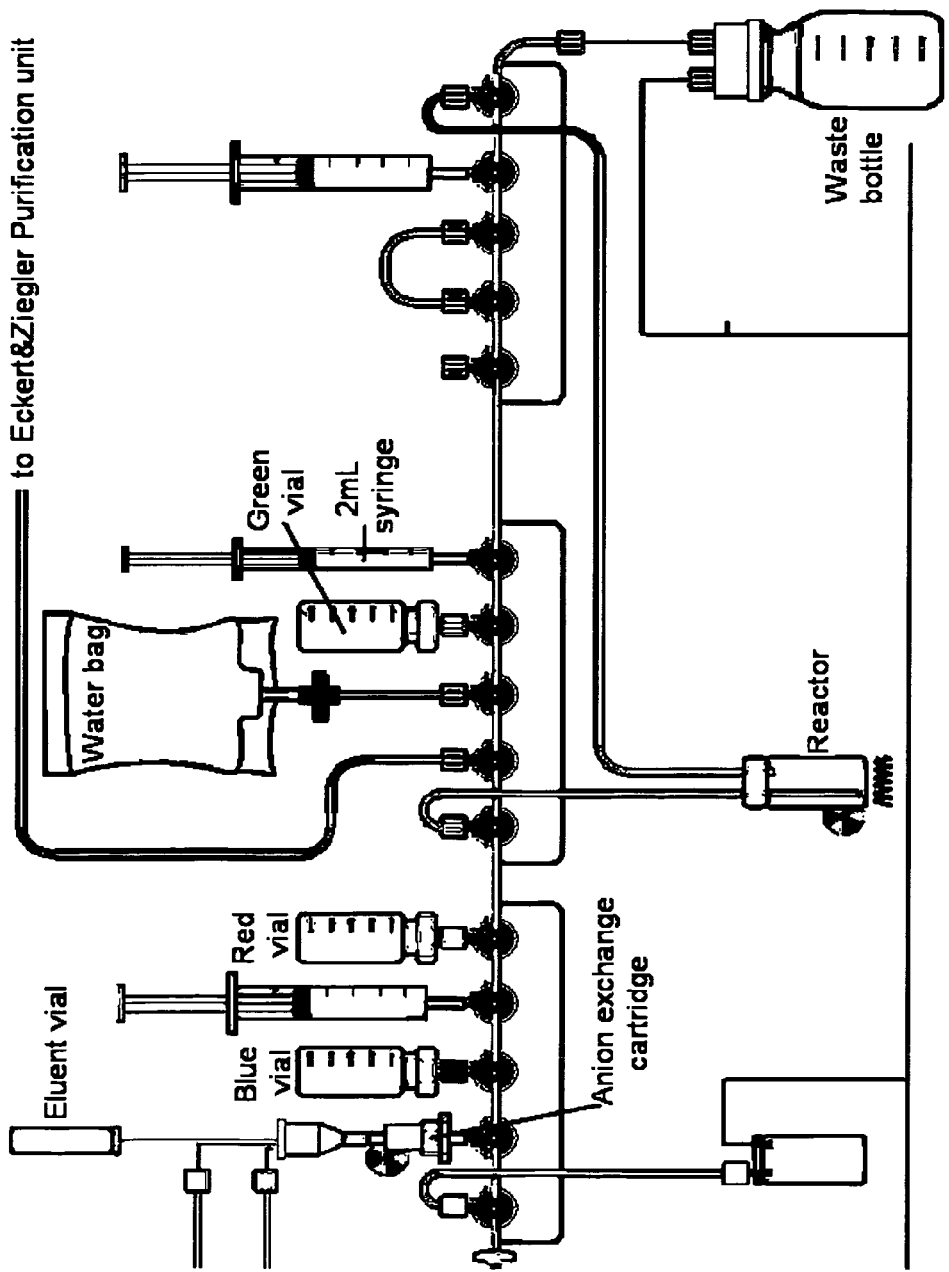
FIG. 5 Setup of Tracerlab MX (adopted from Coincidence FDG software)
Figure 6:
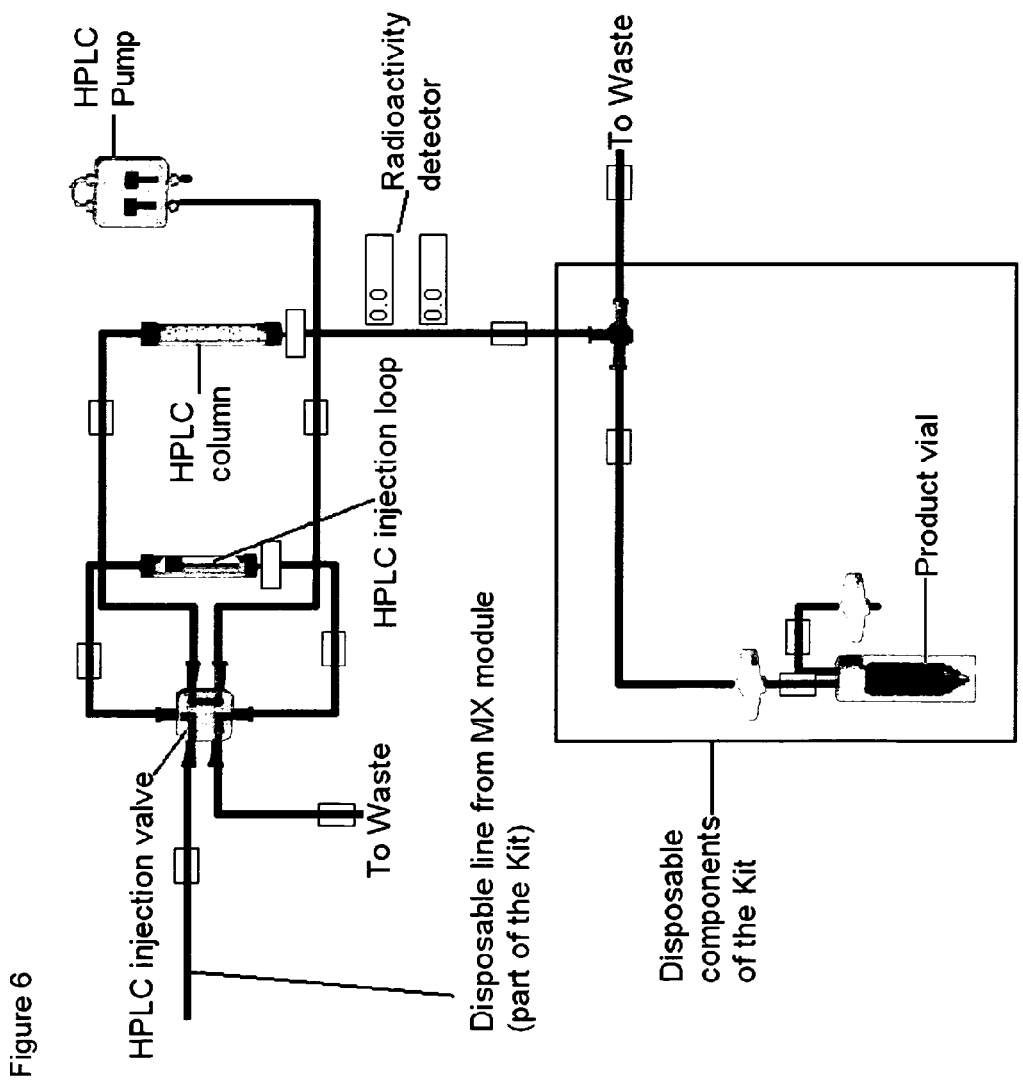
FIG. 6 Setup of Eckert&Ziegler purification unit (adopted from Modual-Lab software)
Figure 7:
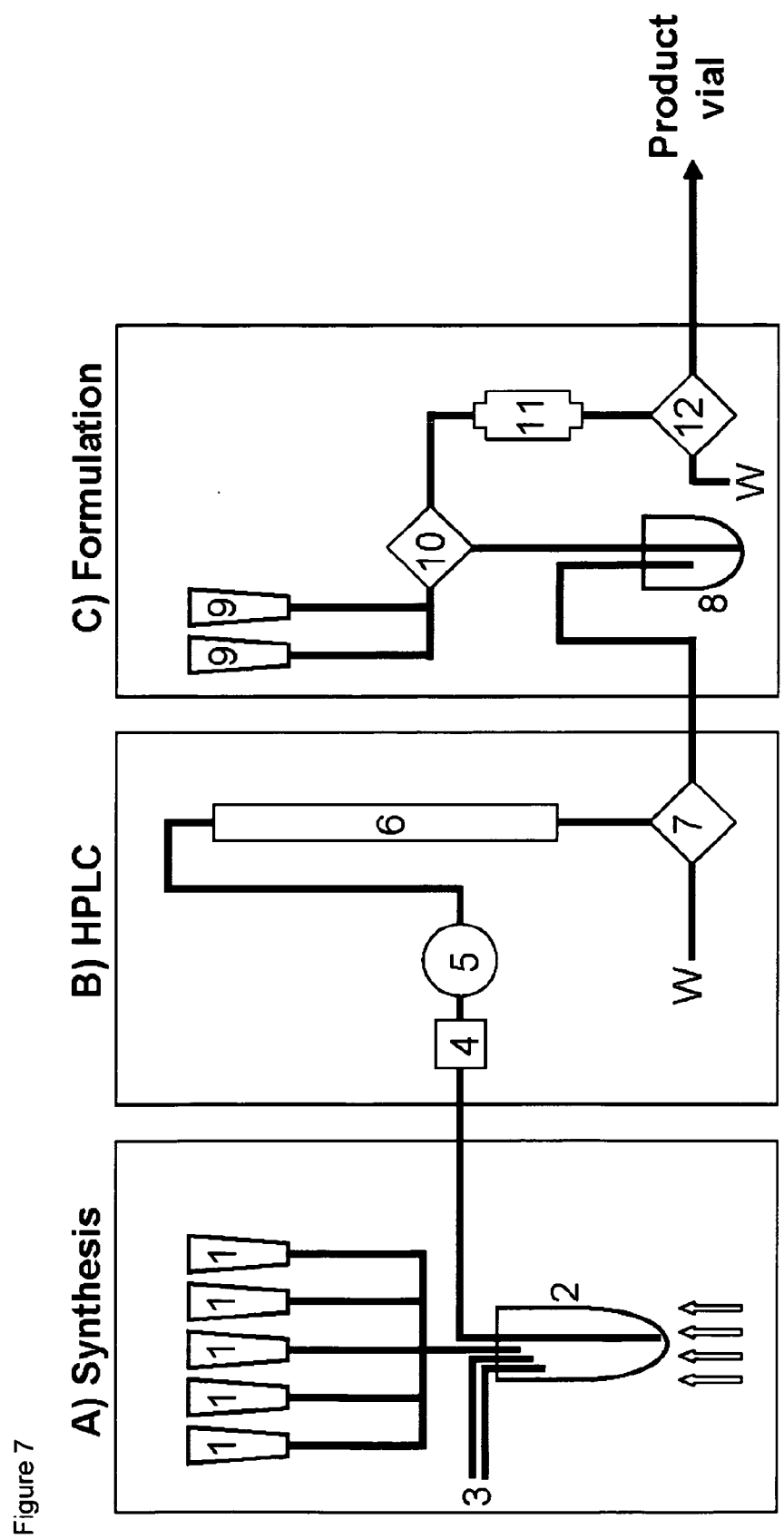
FIG. 7 Schematic illustration of process and equipment for manufacturing of F-18 labeled fluoropegylated (aryl/heteroaryl vinyl)-phenyl methyl amines comprising three parts: A) Synthesis, B) HPLC, C) Formulation; including (1) vials for reagents and solvents, (2) a reaction vessel, (3) target line for F-18, optionally gas lines, vacuum ect., (4) optionally fluid detector or filter ect., (5) injection valve, (6) HPLC column, (7) valve for peak cutting, (W) waste line(s), (8) vessel for collection/dilution of HPLC fraction, (9) solvent vials for washing and elution, (10) valve, (11) cartridge, e.g. C18 cartridge for trapping of the product, (12) valve.
Figure 8:
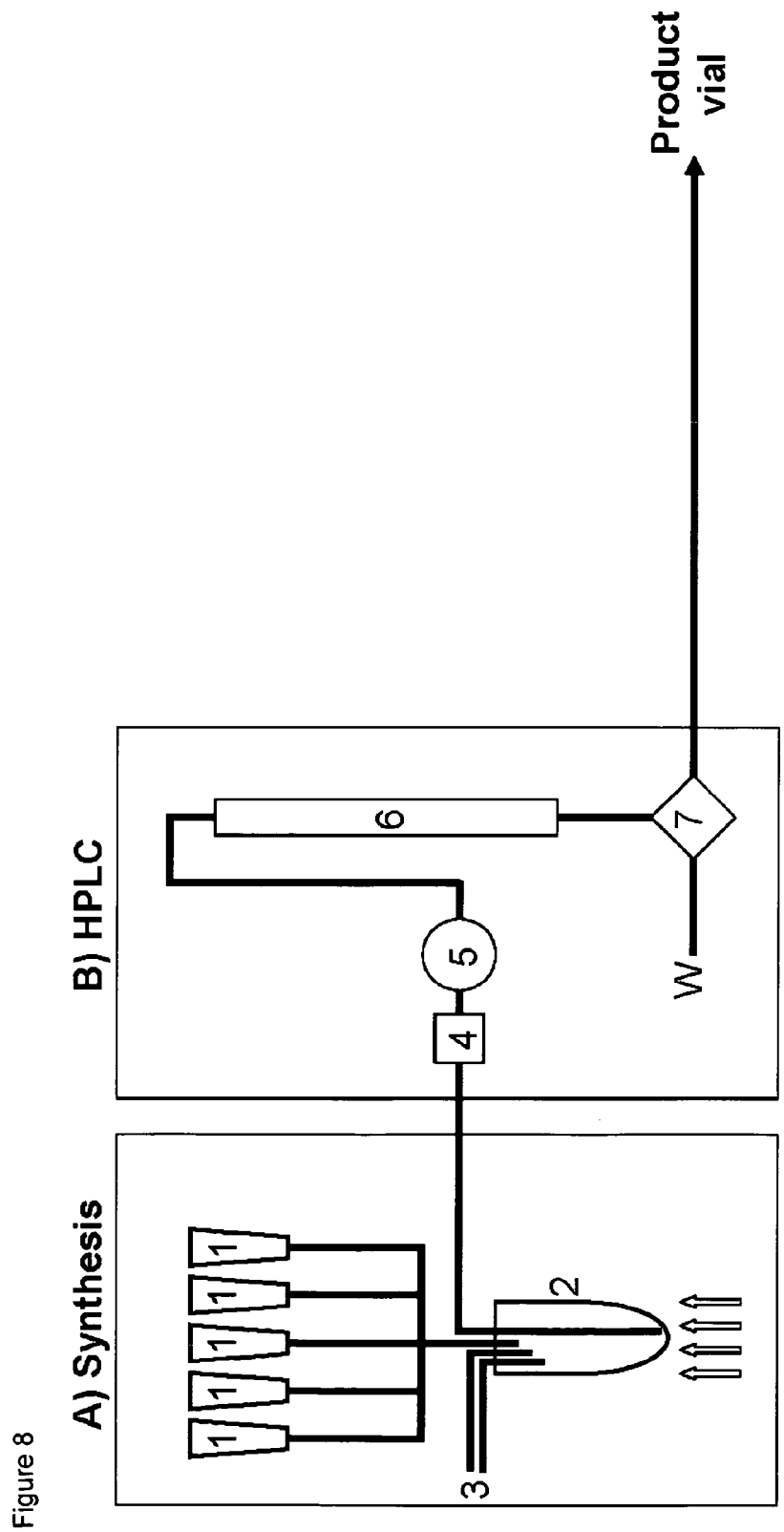
FIG. 8 Schematic illustration of process and equipment for manufacturing of F-18 labeled fluoropegylated (aryl/heteroaryl vinyl)-phenyl methyl amines comprising two parts: A) Synthesis, B) HPLC; including (1) vials for reagents and solvents, (2) a reaction vessel, (3) target line for F-18, optionally gas lines, vacuum ect., (4) optionally fluid detector or filter ect., (5) injection valve, (6) HPLC column, (7) valve for peak cutting.
Figure 9:
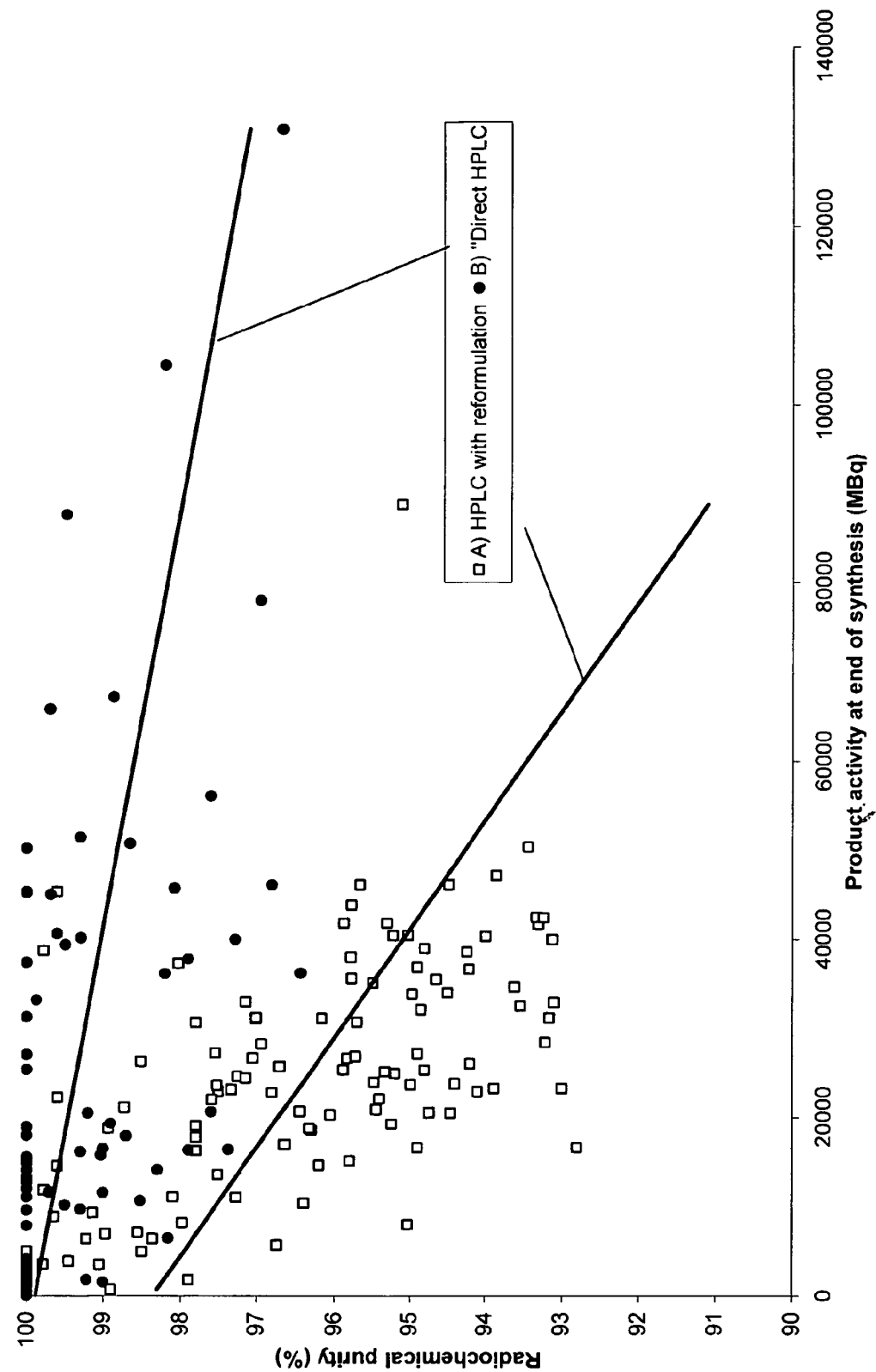
FIG. 9 Influence of purification method on radiochemical purity
Figure 10:
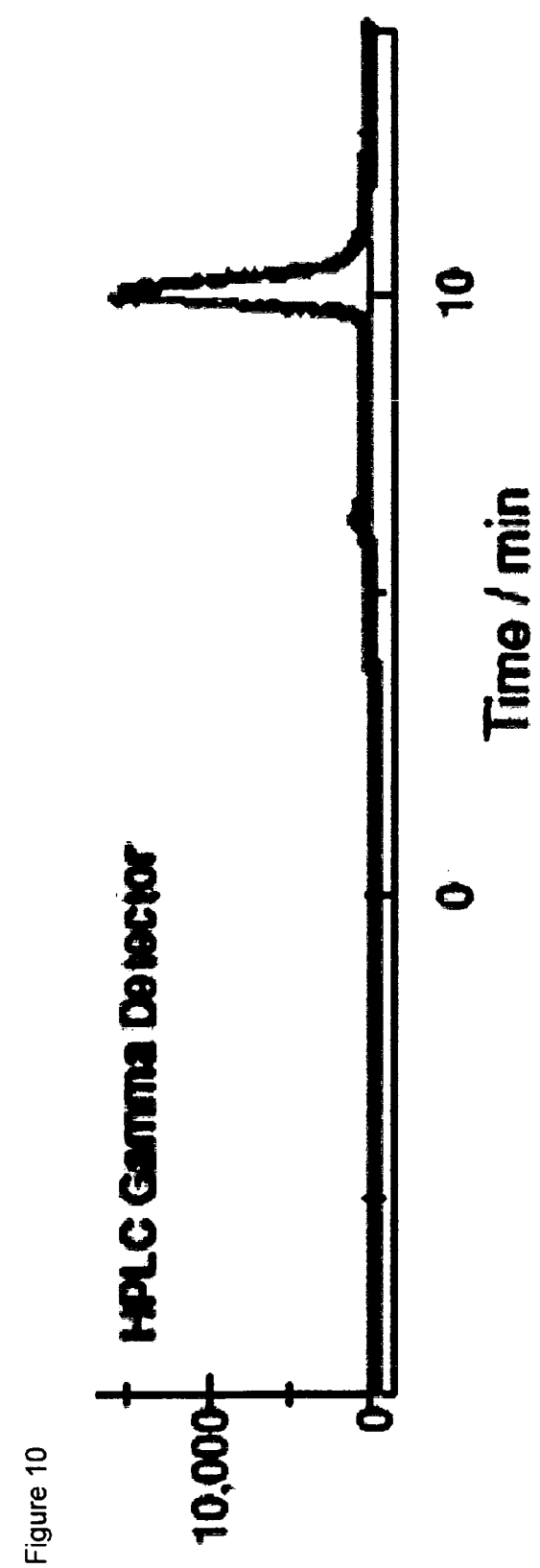
FIG. 10 Chromatogramm of purification of 4-[(E)-2-(6-{2-[2-(2-[F-18]fluoro-ethoxy)ethoxy]ethoxy}pyridin-3-yl)vinyl]-N-methylaniline on Eckert&Ziegler modular lab (Radioactivity channel).

The invention claimed is:
1. A method for producing an injectable formulation of a compound of Formula I suitable for injection into humans

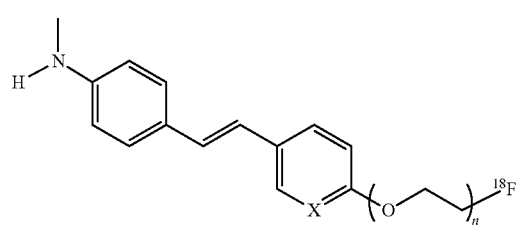

I comprising the steps of:

Step 1: radiolabeling a compound of Formula II with a F-18 fluorinating agent, to obtain a compound of Formula I, if R=H or to obtain compound of Formula III, if R=PG

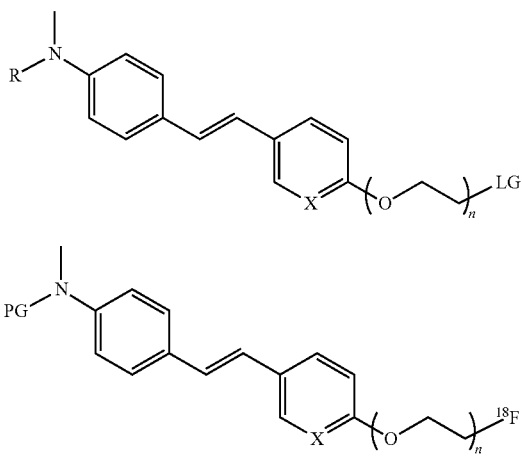

Step 2: if R=PG, cleaving the protecting group PG to obtain a compound of Formula I, and Step 3: purifying and formulating a compound of Formula I wherein:
n=3,
X is selected from the group consisting of
  a) CH, and
  b) N,
R is selected from the group consisting of
  a) H, and
  b) PG,
PG is an amine-protecting group, and
LG is a leaving group,
wherein Step 3 comprises purifying and formulating a compound of formula I using a HPLC separation using an HPLC solvent eluent consisting of an ethanol/aqueous buffer mixture and wherein the fraction obtained from the HPLC purifying is part of an injectable formulation of a compound of formula I suitable for injection into humans, and wherein the radioactive level of the injectable formulation prepared by the method is more than 50 GBq, wherein the radiochemical purity of the injectable formulation prepared by the method is >95%.

2. The method according to claim 1, wherein PG is selected from the group consisting of:
  a) Boc,
  b) Trityl and
  c) 4-Methoxytrityl.

3. The method according to claim 1, wherein LG is selected from the group consisting of:
  a) Halogen and
  b) Sulfonyloxy,
wherein Halogen is chloro, bromo or iodo.

4. The method according to claim 3, wherein LG is Sulfonyloxy and it is selected from the group consisting of:
  a) Methanesulfonyloxy,
  b) p-Toluenesulfonyloxy,
  c) (4-Nitrophenyl)sulfonyloxy, and
  d) (4-Bromophenyl)sulfonyloxy.

5. The method according to claim 1, wherein X=CH.

6. The method according to claim 1, wherein X=CH, R=H or Boc, and LG=Methanesulfonyloxy or p-Toluenesulfonyloxy.

7. The method according to claim 1, wherein the aqueous buffer is a solution of sodium chloride, sodium phosphate buffer, ascorbic acid, ascorbate buffer, or a mixture thereof.

8. The method of claim 1, wherein no re-formulation to remove constituents of the HPLC solvent is performed.

9. The method of claim 1, wherein the collected product fraction after HPLC is not trapped on a solid-phase extraction cartridge.

10. The method of claim 8, wherein the collected product fraction after HPLC is not trapped on a solid-phase extraction cartridge.

11. The method of claim 1, wherein radioactive level of the injectable formulation prepared by the method is more than 100 GBq.

12. The method of claim 1, wherein the HPLC method is conducted only with HPLC solvent or solvent mixture which would be suitable for injection into humans.

13. The method of claim 1, wherein the radiochemical purity of the injectable formulation prepared by the method is >98%.

14. The method of claim 1, wherein the radiochemical purity of the injectable formulation prepared by the method is ≥99%.

* * * * *